United States Patent
Strömme et al.

(12)

(10) Patent No.: US 11,155,469 B2
(45) Date of Patent: Oct. 26, 2021

(54) MESOPOROUS COMPOSITE COMPRISING ANHYDROUS, AMORPHOUS MAGNESIUM CARBONATE AND CALCIUM CARBONATE, AND METHODS OF PRODUCTION THEREOF

(71) Applicant: DISRUPTIVE MATERIALS AB, Uppsala (SE)

(72) Inventors: Maria Strömme, Uppsala (SE); Albert Mihranyan, Uppsala (SE); Johan Gómez De La Torre, Uppsala (SE); Sara Frykstrand Ångström, Sollentuna (SE)

(73) Assignee: Disruptive Materials Operations AB, Uppsala (SE)

( * ) Notice: Subject to any disclaimer, the term of this patent is extended or adjusted under 35 U.S.C. 154(b) by 0 days.

(21) Appl. No.: 16/658,281

(22) Filed: Oct. 21, 2019

(65) Prior Publication Data

US 2020/0048104 A1     Feb. 13, 2020

Related U.S. Application Data

(63) Continuation of application No. 15/430,570, filed on Feb. 13, 2017, now Pat. No. 10,508,041, which is a
(Continued)

(51) Int. Cl.
*B32B 5/16* (2006.01)
*C01F 5/02* (2006.01)
(Continued)

(52) U.S. Cl.
CPC ............... *C01F 5/02* (2013.01); *A23L 33/16* (2016.08); *A61K 8/19* (2013.01); *A61K 31/192* (2013.01);
(Continued)

(58) Field of Classification Search
CPC .................................. C01F 5/24; C01F 11/18
(Continued)

(56) References Cited

U.S. PATENT DOCUMENTS 2,186,040 A     1/1940   Plumstead
2,802,720 A     8/1957   Opatowski
(Continued)

FOREIGN PATENT DOCUMENTS

EP     1 475 351 A1     11/2004
EP     2206681 A2       7/2010
(Continued)

OTHER PUBLICATIONS

Frykstrand et al., On the pore forming mechanism of Upsalite, a micro- and mesoporous magnesium carbonate, Microporous and Mesoporous Materials, vol. 190, May 15, 2014, pp. 99-104. https://doi.org/10.1016/j.micromeso.2013.12.011 (Year: 2014).*
(Continued)

*Primary Examiner* — Hoa (Holly) Le
(74) *Attorney, Agent, or Firm* — Morgan, Lewis & Bockius LLP

(57) ABSTRACT

An X-ray amorphous magnesium carbonate is disclosed that is characterized by a cumulative pore volume of pores with a diameter smaller than 10 nm of at least 0.018 cm$^3$/g, and a specific surface areas of at least 60 m$^2$/g. The X-ray amorphous magnesium carbonate is produced by reacting an inorganic magnesium compound with alcohol in a $CO_2$ atmosphere. The X-ray amorphous magnesium carbonate can be a powder or a pellet and acts as a desiccant in, for example, production of food, chemicals or pharmaceuticals.

21 Claims, 18 Drawing Sheets

Related U.S. Application Data continuation of application No. 14/648,780, filed as application No. PCT/IB2013/060647 on Dec. 4, 2013, now Pat. No. 9,580,330.

(60) Provisional application No. 61/734,144, filed on Dec. 6, 2012.

(51) Int. Cl.

| | | |
|---|---|---|
| *A61Q 19/00* | (2006.01) | |
| *B01J 41/14* | (2006.01) | |
| *B01J 45/00* | (2006.01) | |
| *B01J 20/26* | (2006.01) | |
| *B01J 20/28* | (2006.01) | |
| *A23L 33/16* | (2016.01) | |
| *A61K 47/02* | (2006.01) | |
| *A61K 8/19* | (2006.01) | |
| *C01F 5/24* | (2006.01) | |
| *A61K 31/192* | (2006.01) | |
| *B01J 20/04* | (2006.01) | |
| *A61K 9/14* | (2006.01) | |

(52) U.S. Cl.
CPC .............. *A61K 47/02* (2013.01); *A61Q 19/00* (2013.01); *B01J 20/043* (2013.01); *B01J 20/267* (2013.01); *B01J 20/28011* (2013.01); *B01J 20/28019* (2013.01); *B01J 20/28059* (2013.01); *B01J 20/28061* (2013.01); *B01J 20/28064* (2013.01); *B01J 20/28066* (2013.01); *B01J 20/28071* (2013.01); *B01J 20/28083* (2013.01); *B01J 41/14* (2013.01); *B01J 45/00* (2013.01); *C01F 5/24* (2013.01); *A23V 2002/00* (2013.01); *A61K 9/143* (2013.01); *A61K 2800/10* (2013.01); *C01P 2002/02* (2013.01); *C01P 2002/72* (2013.01); *C01P 2002/74* (2013.01); *C01P 2002/82* (2013.01); *C01P 2002/85* (2013.01); *C01P 2002/88* (2013.01); *C01P 2004/03* (2013.01); *C01P 2006/12* (2013.01); *C01P 2006/14* (2013.01); *C01P 2006/16* (2013.01); *C01P 2006/17* (2013.01); *Y02C 20/40* (2020.08)

(58) Field of Classification Search
USPC ................................ 423/155, 165, 430, 432
See application file for complete search history.

(56) References Cited

U.S. PATENT DOCUMENTS

| | | | |
|---|---|---|---|
| 4,808,654 A | | 2/1989 | Rolfe et al. |
| 5,240,692 A | * | 8/1993 | Morifuji .................. C01F 5/24 423/430 |
| 9,580,330 B2 | * | 2/2017 | Stromme ........... B01J 20/28083 |
| 10,508,041 B2 | * | 12/2019 | Stromme ................. B01J 45/00 |
| 2005/0129606 A1 | | 6/2005 | Mitsuhashi et al. |
| 2010/0178227 A1 | | 7/2010 | Kim et al. |
| 2017/0152151 A1 | | 6/2017 | Strömme et al. |

FOREIGN PATENT DOCUMENTS

| | | |
|---|---|---|
| JP | S54-057000 A | 5/1979 |
| JP | S64-047423 A | 2/1989 |
| JP | 2004-203700 A | 7/2004 |
| JP | 2005-154158 A | 6/2005 |
| JP | 2007-254193 A | 10/2007 |

OTHER PUBLICATIONS

Neuberg et al., "Ueber kolloide und gelatinbse Verbindungen der Erdalkalien", Zeitschrift für Chamie und Industrie Der Kolloide, vol. 2, No. 12, Jun. 1908, pp. 354-357.

International Search Report and Written Opinion dated May 15, 2014, for International application No. PCT/IB2013/060647.

First Office Action for Chinese Application No. 201380063695.1 dated Apr. 12, 2016.

International Preliminary Report on Patentability and Written Opinion dated Jun. 9, 2015, for International Application PCT/IB2013/060647.

Office Action for Eurasian Application No. 201590901 dated May 31, 2016.

Scott et al., "Magnesite formation from MgO and CO2 at the pressures and temperatures of Earth's mantle", American Mineralogist, vol. 98, 1211-1218 (2013).

Communication pursuant to Article 94(3) EPC dated Jan. 4, 2017, for corresponding European patent application No. 13808233.4.

Office Action issued in corresponding Indian Patent Application No. 3913/CHENP/2015, dated Nov. 8, 2018.

Fricker & Park, "Effect of H2O on Mg(OH)2 carbonation pathways for combined CO2 capture and storage", Chemical Engineering Science 100 (2013) 332-341 (Year: 2013).

Meyer and Klobes, "Comparison between different presentations of pore size distribution in porous materials", Fresenius J Anal Chem (1999) 363: 174-178 (Year: 1999).

Office Action dated Oct. 24, 2017, issued in corresponding Japanese Patent Application No. 2015-546135.

Schaef et al., "Brucite[Mg(OH2)] carbonation in wet supercritical CO2: an in situ high pressure X-ray diffraction study", Geochimica et Cosmochimica Acta 75 (2011) 7458-7471.

Ohkubo et al., "Preparation of petaloid microspheres of basic magnesium carbonate", Langmuir (2007), 23, 5872-5874.

\* cited by examiner

MESOPOROUS COMPOSITE COMPRISING ANHYDROUS, AMORPHOUS MAGNESIUM CARBONATE AND CALCIUM CARBONATE, AND METHODS OF PRODUCTION THEREOF

RELATED APPLICATION DATA

This application is a continuation application of U.S. application Ser. No. 15/430,570, filed Feb. 13, 2017, which is a continuation application of U.S. application Ser. No. 14/648,780, filed Jun. 1, 2015, which is a § 371 National Stage Application of PCT International Application No. PCT/IB2013/060647, filed Dec. 4, 2013, which is based on and claims priority to U.S. Provisional Patent Application No. 61/734,144, filed Dec. 6, 2012, the entire contents of each are incorporated herein by reference.

FIELD OF INVENTION

The present invention relates to an amorphous, anhydrous, micro porous magnesium carbonate with large specific surface areas and extraordinary moisture sorption properties and to a method of forming such. The invention further relates to, but is not limited to: dehumidifiers, moisture control, vacuum insulation panel and thermochemical energy storage materials, delivery or carrier systems for therapeutic and cosmetic or volatile agents, odour control, sanitation after fire or fire retardants, as well as to materials for collection of toxic waste, chemicals or oil spill and to materials for pest control and for protection of crops and food stuff.

BACKGROUND OF THE INVENTION

In the discussion that follows, reference is made to certain structures and/or methods. However, the following references should not be construed as an admission that these structures and/or methods constitute prior art. Applicant expressly reserves the right to demonstrate that such structures and/or methods do not qualify as prior art against the present invention.

Magnesium is the eighth most abundant element in the earth's crust and essential to most living species. It can form several forms of hydrated carbonates such as nesquehonite ($MgCO_3 \cdot 3H_2O$), and lansfordite ($MgCO_3 \cdot 5H_2O$), a number of basic carbonates such as hydromagnesite ($4MgCO_3 \cdot Mg(OH)_2 \cdot 4H_2O$), and dypingite ($4MgCO_3 \cdot Mg(OH)_2 \cdot 5H_2O$) as well as the anhydrous and rarely encountered magnesite ($MgCO_3$). The various forms of magnesium carbonate are all industrially important materials and for example used in pharmaceutics as antacids, adsorbents and diluents in direct compression tablets. They are also found in cosmetics thanks to their mild astringent properties which help to smoothen and soften skin, and have found their applications in dusting powders, face masks as well as in toothpastes. In addition, high purity magnesium carbonates are useful desiccants, for instance, as an additive in table salt to keep it free flowing or as a drying agent for hands to improve the grip, e.g. for rock climbing, gymnastics, and weight lifting.

Commercial (crystalline) analogues of magnesium carbonates typically show specific surface areas (SSAs) of about 4-18 $m^2\ g^{-1}$. For previously reported X-ray amorphous magnesium carbonates produced by thermal decomposition of hydrated magnesium carbonates forms, the highest SSA found in the literature is ~50 $m^2\ g^{-1}$.

For many geologists, the anhydrous (native) magnesite is a conspicuous rock with unclear genesis. Although magnesium carbonates are abundant in nature in the form of minor traces in most geological structures, magnesium carbonate rarely exists as a monomineralic magnesite in economically viable deposits. In fact, there are virtually only two types of magnesite deposits in the world: the sparry magnesite of Vietsch type, which constitutes 90% of world's reserves and forms nearly monomineralic lenses within marine platform sediments, and the less common but highly valued Kraubath type magnesite of superior quality. The Kraubath type consists of veins (300-400 meter deep) and stockworks (80 meter deep) of cryptocrystalline "bone" magnesite, also sometimes referred to as gel-magnesite. It commonly occurs together with ultramafic rock structures such as serpentine (($Mg,Fe)_3Si_2O_5(OH)_4$) and olivine (($Mg,Fe)_2SiO_4$) minerals. The formation of Kraubath type magnesite is suggested to occur through a so-called epigenetic-hydrothermal route, wherein hydrothermal fluids of moderate temperature and low salinity carrying $CO_2$ interact with ultramafic rocks. Most of the silica and iron derived from the decomposition of ultramafic rocks are carried to the surface whereas the veins of magnesite precipitate in situ as a gel.

In nature, magnesium carbonate occurs in two physical forms; as macrocrystalline or cryptocrystalline magnesite. The cryptocrystalline form is also sometimes referred to as amorphous or gel magnesite by geologists, however, it should be stressed that this does not imply that it is X-ray amorphous, merely that the size of the crystallites are too small to be observe with a light microscope. Hereinafter the term amorphous should be interpreted to mean X-ray amorphous.

X-ray amorphous magnesite has been observed upon thermal decomposition of crystalline hydrated magnesium carbonates occurring at temperatures of the order of 300° C. or higher. Such magnesites are, however, not stable upon long term storage in humid atmosphere as it has been shown that the carbonate bond is weakened during rehydration. This weakening is evident by the fact that the decarbonation peak in differential Thermogravimetic measurement (dTGA) curves at about 350° C. or above develops a shoulder and/or splits into two or more peaks and also shifts towards lower temperatures.

Interestingly, magnesite has stirred problems not only for the geologists but also for the chemists. Anhydrous $MgCO_3$ can easily be produced at elevated temperatures. However, numerous authors, have described unsuccessful attempts to precipitate anhydrous magnesium carbonate from a magnesium bicarbonate solution kept at room temperature and under atmospheric pressure. Instead, hydrated magnesium carbonates or one of the more complex basic magnesium carbonates precipitated under such conditions leading to what has been branded as "the magnesite problem".

In 1999, successful attempts of making crystalline magnesite at 400° C. and atmospheric pressure was presented by using a suspension of artificial sea-water with calcium carbonate and urea through which $CO_2$ was bubbled followed by dissolution and titration with dilute ammonia during which carbonate precipitated. The precipitate was characterized as crystalline magnesite using X-ray diffraction, and traces of aragonite ($CaCO_3$) and possibly calcite ($CaCO_3$) were noted in the diffractogram. The experiment has since been repeated and the precipitates consisted of magnesite with traces of aragonite ($CaCO_3$) and dypingite ($Mg_5(CO_3)_4(OH) \cdot 5H_2O$). In both of the experiments magnesite was formed after 14 dissolution-precipitation cycles.

It should be mentioned that magnesium carbonate was attempted to be synthesized also in non-aqueous solvents during the early 1900's. However, it was concluded that magnesium carbonate cannot be obtained by passing $CO_2$ gas through methanolic suspensions of MgO due to the more likely formation of magnesium dimethyl carbonate $Mg(OCO)(OCH_3)_2$.

Subsequent studies only reiterated the assumption that MgO preferentially forms complex dimethyl carbonates when reacted with $CO_2$ in methanol. This conclusion was especially peculiar since carbonates of other rare earth metals, such as those of Ca, Ba, and Sr, can be readily produced by passing $CO_2$ gas through alcoholic suspensions of their respective oxides.

In view of the above-mentioned industrial applications of magnesium carbonates and their non-toxic properties, further improvements in the magnesium carbonates and their production methods are desirable to allow for expanded use of magnesium carbonates in various applications. As well, introduction of a new class of magnesium carbonate containing materials with structural and functional properties that have currently not been found in previously disclosed magnesium carbonate containing materials are foreseen to open up for new industrial applications and for improved functionality in already existing applications. To become industrially attractive, areas of improvements include water sorption properties, porosity, specific surface area, long term stability of the material and the cost of production.

There are, to our knowledge, no prior art disclosing a magnesium carbonate material containing micro and/or meso pores, neither among the reports describing crystalline magnesium carbonates nor the X-ray amorphous ones produced by thermal decomposition. A nitrogen sorption analysis performed on, e.g., hydromagnesite ($Mg_5(CO_3)_4(OH)_2 \cdot 5H_2O$)), which is the pharmaceutical grade of magnesium carbonate, reveals a material with no porosity in the micro pore range and with some meso pores between, but not inside, the powder particles, as will become evident in the drawings and examples that follows.

Magnesium carbonates are well known for their desiccant properties in applications like those mentioned above, e.g., for keeping table salt free flowing in humid climates and as gripping agents in rock climbing. Existing magnesium carbonate majorly adsorbs moisture around or above 70% relative humidity (RH) at room temperature and are not know to be good moisture adsorbents at low RHs.

The stability of presently known amorphous and anhydrous magnesium carbonates, i.e. those produced by thermal decomposition of crystalline hydrated magnesium carbonates, are known to be limited upon storage in humid environments. The carbonate bond of such materials usually weakens after only 2 weeks of storage in 100% humidity, preventing a regeneration of the materials original structure and properties.

SUMMARY OF THE INVENTION

It is an object of the present invention to provide a novel group of magnesium carbonate based materials with improved properties with regards to, for example, surface area, micro and meso pore volume, moisture sorption properties and regeneration properties as well as storage stability as compared to other carbonates as well as to other classes of materials used for, e.g., moisture sorption and drug delivery, as well as other applications exemplified herein. It is a further object to provide methods of producing such magnesium carbonate based materials, which are industrially feasible.

Herein micro pores, refers to pores with a diameter less than 10 nm and meso pores refers to pores with diameters between 10 and 100 nm, instead of the traditionally used range of 2-50 nm. Accordingly, micro porous refers to a material comprising micro pores with a diameter less than 10 nm and meso porous refers to a material comprising meso pores with a diameter between 10 nm and 100 nm.

Surprisingly, we have found that anhydrous, amorphous, micro porous, high specific surface area magnesium carbonate with unique moisture sorption properties at low RHs can be produced at low temperatures from a Mg-containing precursor, like MgO, in organic solvents. The magnesium carbonate produced can be either in the form of suspension, gel or powder. The produced magnesium carbonate has a surface area much larger than that reported for any other magnesium carbonate material and comprises a substantial portion of micro pores, i.e. a cumulative volume of pores with a diameter smaller than 10 nm in the range 0.018-3 $cm^3/g$. The novel material is stable upon storage at high RHs for prolonged time periods, in contrast to earlier described amorphous magnesium carbonate materials. Further, we have also found that the produced magnesium carbonate has excellent moisture sorption properties, especially at low RHs, which are highly favorable in a number of industrial applications. These and other advantages of the material are described in detail below. The introduction of a new class of magnesium carbonate containing materials with structural and functional properties that have currently not been found in previously disclosed magnesium carbonate containing materials are foreseen to open up new industrial applications and improved functionality in already existing applications.

The magnesium carbonate according to the invention is X-ray amorphous, anhydrous, exhibits a cumulative volume of pores with a diameter smaller than 10 nm of at least 0.018 $cm^3/g$, preferably of at least 0.4 $cm^3/g$, and even more preferably of at least 0.8 $cm^3/g$, and a cumulative volume of pores with a diameter smaller than 10 nm up to 1.5 $cm^3/g$, or more preferably up to 2 $cm^3/g$ or most preferably up to 3 $cm^3/g$. As appreciated by the skilled person, the unique distribution of micro and meso pores according to the present invention can be described with other parameters and can be based on other types of measurements than described herein.

Such pore volume should be determined by Density Functional Theory (DFT) analysis of nitrogen sorption isotherms, wherein the pore size distribution is derived from the nitrogen isotherm using the DFT method assuming a slit-shaped pore model. The magnesium carbonate according to the invention further exhibits a specific surface areas (SSAs) of at least 60 $m^2/g$, preferably of at least 100 $m^2/g$, more preferably of at least 240 $m^2/g$, even more preferably of at least 350 $m^2/g$, most preferably of at least 600 $m^2/g$, and a SSA up to 400 $m^2/g$, preferably up to 800 $m^2/g$, more preferably up to 1000 $m^2/g$, even more preferably up to 1200 $m^2/g$ and most preferably up to 1500 $m^2/g$. The specific surface area can be determined from a BET analysis of nitrogen adsorption isotherms.

The method according to the invention of producing the high SSA, porous, amorphous and anhydrous magnesium carbonate, comprises reacting an inorganic magnesium compound, for example MgO, with alcohol in a $CO_2$ atmosphere. The pressure should preferably be 1-3 bar, and the temperature 40° C. to boiling temperature of the liquid. The method may be realized by the steps:

[Step 1] Mixing a Mg-containing precursor and an alcohol-containing liquid in a reactor, the mixing is preferable performed under continuous stirring and the consistency of the mixture is preferably of liquid character. During this step, the ingredients in the mixture react to form one or several intermediates that later can interact with $CO_2$.

the mixture is preferably heated in order to facilitate reactions between the ingredients in the mixture. Temperatures between 40° C. and boiling temperature of the liquid are preferable for the reaction to occur, however lower temperatures down to the freezing temperature of the liquid is enough for a less complete reaction.

typically about 3 h to 24 h at 50° C. for liquid volumes of 100 to 3000 ml.

[Step 2] Reacting the mixture with $CO_2$. In this step, the intermediate products formed during step 1 interact with $CO_2$ to form one or several types of carbonated intermediate products.

this step can be performed at temperatures ranging from the freezing temperature to the boiling temperature of the liquid, and at $CO_2$ pressures ranging from 0.001 to 200 bar above atmospheric pressure. However, temperatures below 30° C. and pressures below 5 bar are beneficial for carbonation of the intermediate products.

during this step, the carbonated intermediate products can form a gel in the reactor, typically this occurs after 4-6 days if the $CO_2$ pressure is 1 bar and the temperature is 20° C. during step 2.

[Step 3] Solidification and drying of the material.

the liquid or gel formed in the reactor during step 2 is dried in order to obtain a solid material and the carbonated intermediate products formed during step 2 are transformed into anhydrous magnesium carbonate.

temperatures between 60° C. and 300° C.

depending on the intermediates formed during step 1 and 2, presence of water during the step can facilitate the transformation to magnesium carbonate via hydrolysis.

the drying and solidification process in may include techniques such as spray drying or oven drying.

Thanks to the present invention it is possible to provide an amorphous, anhydrous, micro porous and high surface area magnesium carbonate which is stable upon storage for months or longer, at room temperature and relative humidity at least above 60%. The novel material exhibit extraordinary moisture sorption properties, especially at low RHs, and is comparable, or even superior, to those of hydrophilic zeolites, e.g. zeolite Y (600 $m^2$ $g^{-1}$, silica/alumina ratio 5.2:1) and also superior to those of commonly used dessicants, e.g. fumed silica (Aerosil) or crystalline hydromagnesite. As measured using an ASAP 2020 from Micromeritics equipped with a water vapor source, the novel magnesium carbonate material adsorbs more than 0.6 mmol water/g material, preferably more than 0.7 mmol water/g material, even more preferably more than 1 mmol or 2 mmol water/g material, most preferably more than 3 mmol water/g material at an RH of 3% at room temperature. It adsorbs more than 1.5 mmol water/g material, preferably more than 1.7 mmol water/g material, even more preferable more than 2 mmol water/g material, most preferably more than 4 or 5 mmol water/g material at an RH of 10% at room temperature and adsorbs more than 10 mmol water/g material, more preferably more than 14 mmol water/g material, most preferably more than 20 mmol water/g material at an RH of 90% at room temperature. Also the moisture retention ability and regeneration properties are extraordinary; experiments have verified that the novel magnesium carbonate material retains more than 80 wt % of the adsorbed moisture when the RH is lowered from 90% to 5% during a water vapor desorption analysis performed at room temperature. Experiments have further verified that the novel magnesium carbonate material retains more than 90 wt % of the adsorbed moisture when the RH is lowered from 90% to 20% during a water vapor desorption analysis performed at room temperature. Additional experiments have shown that the moisture sorption properties of the novel magnesium carbonate material can be regenerated after storing the material at RH higher than 90% RH for at least 7 days at room temperature by drying the material at only 95° C. during less than 24 hours.

The amorphous, anhydrous, micro porous and high surface area magnesium carbonate according to the invention may be provided as a mixture or composite with other materials, for example for the purpose of tailoring certain properties. As appreciated by the skilled person unavoidable impurities and intermediate products may be present in the final product. The remaining part of the material may be any amorphous or crystalline, organic or inorganic element or compound. Non limiting examples of such other material include salts, like calcium carbonates, crystalline magnesium carbonates, sodium chloride, magnesium nitrate, copper sulfate, hydroxyapatite, strontium acetate, zinc citrate, hydroxides like magnesium hydroxide, strontium hydroxide and silicon hydroxide, oxides like magnesium oxide, iron oxide, silicon dioxide, aluminum oxide, aluminosilicate, metals like gold, silver, zinc, aluminum, as well as organic compounds like cellulose, spider silk and synthetic polymers.

According to one aspect of the present invention the magnesium carbonate of the present invention is produced and used as a functional material in dehumidification procedures. A non-limiting example of such dehumidification procedures includes sorption dehumidification to dehumidify the air in a so-called drum dehumidifier. In such processes, the humid air may enter through a rotor containing the magnesium carbonate of the present invention or a composite thereof that acts as a desiccant in the dehumidifier, and exits as a dry air. The magnesium carbonate of the present invention or a composite thereof can also be fixed on a porous matrix in the rotor in order to increase the airflow through the rotor; this porous matrix can for example be produced from paper. To regenerate the material, warm (e.g. temperatures between 70 and 300° C.) air is blown through a part of the rotor.

According to a further aspect of the invention the magnesium carbonate of the present invention or composites thereof is used as dehumidifying agent for organic solvents. The solvents may be selected from but are not limited to acetone, acetonitrile, benzol, chloroform, cyclohexane, diethylether, dichlormethane, diisopropylether, dimethylformamide, dioxane, ethylester of acetic acid, methylester of acetic acid, ethanol, n-hexane, methanol, isopropanol, pyridine, tetrahydrofurane, toluol, xylol.

According to a yet another aspect of the invention magnesium carbonate of the present invention or composites thereof is used as anti-caking agents to keep powders free flowing in production lines and in products under moist conditions. The magnesium carbonate of the present invention or composites thereof renders its action by dehumidification of the powder bed. Typical examples include, but are not limited to, production lines in food, pharmaceutical and polymer industries, as well as products such as table salt and flour.

According to a yet another aspect of the invention magnesium carbonate of the present invention or non-toxic composites thereof is used as a pharmaceutical additive to improve the powder flow during tableting.

According to a yet another aspect of the invention the magnesium carbonate of the present invention or non-toxic composites thereof is used as a porous pharmaceutical carrier for active pharmaceutical ingredients. The carrier is particularly useful to improve the apparent solubility of poorly soluble Type II and Type IV drugs according to BSC classification. The material of the present invention may also be used as a pharmaceutical additive which protects moisture-sensitive drugs from degrading.

A further aspect of the present invention includes the production and use of the magnesium carbonate of the present invention or composites thereof in pharmaceutical formulations as an excipient in order to protect moisture sensitive substances from contact with moisture. The magnesium carbonate will act as a moisture sink in the formulation and adsorb moisture present in the formulation.

One aspect of the present invention includes the production and use of the magnesium carbonate of the present invention or composites thereof as a material which is useful as a hand drying agent and a material improving the grip for sports and recreation, including weight lifting and climbing.

Yet another aspect of the present invention includes the production and use of the magnesium carbonate of the present invention or composites thereof as a material for drying packages, containers, cargo etc. during transportation and storage.

Another aspect of the present invention includes the production and use of the magnesium carbonate of the present invention or composites thereof as porous filler material in vacuum insulation panels used for thermal and/or acoustic insulation.

Another aspect of the present invention includes the production and use of the magnesium carbonate of the present invention or composites thereof in thermochemical energy storage device which utilizes the energy released due to water vapor adsorption. Such thermochemical energy storage is particularly useful in electric appliances including, but not limited to, dishwashers, refrigerators and climate control equipment.

In an additional aspect of the present invention the magnesium carbonate of the present invention or composites thereof are produced and used in agriculture applications. A non-limiting example of such applications includes the use of the magnesium carbonate of the present invention or composites thereof as a carrier of essential oils for pest control. The insect or bug repellant oils are stabilized and slowly released from the porous carriers in order to achieve a long-term repellant effect.

Another aspect of the present invention includes the production and use of the magnesium carbonate of the present invention or composites thereof to protect crops, and other types of food stuff, in bulk storages against insects, bugs and other unwanted organisms by utilizing the dehumidifying action of the magnesium carbonate of the present invention. The insects, bugs, pest and other unwanted organisms are selected from but not limited to beetles, flies, weevils, worms, moths, mold and cockroaches.

Yet another aspect of the present invention includes the production and use of the magnesium carbonate of the present invention or composites thereof to expelling insects, bug and other unwanted organisms from houses, buildings and storage rooms/containers by utilizing the dehumidifying action of the magnesium carbonate of the present invention.

A further aspect of the present invention includes the production and use of the magnesium carbonate of the present invention or composites thereof is in microbial and probiotic formulations preventing moisture to affect the active components in the formulations. By acting as a moisture sink, the magnesium carbonate can stabilize the formulation, minimize the amount of available moisture that can affect the active components, and hinder degradation of the same.

A further aspect of the present invention includes the production and use of the magnesium carbonate of the present invention or composites thereof as an oil, fat or sweat adsorbing agent in cosmetics and cosmeceuticals included but not limited to dry shampoos, face and body powders, formulations to treat or prevent acne, formulations for eczema prone skin. Herein and below the term cosmeseutical refers to the combination of cosmetics and pharmaceuticals. Cosmeceuticals are, thus, cosmetic products with biologically active ingredients purporting to have medical or drug-like benefits.

A further aspect of the present invention includes the production and use of the magnesium carbonate of the present invention or composites thereof for delivery of moisture, oil or fat to skin when the material is used in skin moisturizer products.

A further aspect of the present invention includes the production and use of the magnesium carbonate of the present invention or composites thereof as a cleansing agent that adsorbs impurities from the skin, as well as acts as an astringent and helps to close pores.

A further aspect of the present invention includes the production and use of the magnesium carbonate of the present invention or composites thereof for delivery of fragrances where the magnesium carbonate of the present invention or composites thereof acts as a carrier for the fragrances. Typical applications are selected from but not limited to cosmetics, perfumes, skin-care products and products for odour control in domestic environments, cars, warehouses, industry buildings, waste disposal sites, sewage plants and public toilets.

A further aspect of the present invention includes the production and use of the magnesium carbonate of the present invention or composites thereof to improve the ability for cosmetic products to take up moisture.

Yet another aspect of the present invention includes the production and use of the magnesium carbonate of the present invention or composites thereof for air sanitation through uptake/adsorption of molecules causing undesired smells where the magnesium carbonate of the present invention or composites thereof acts as an adsorbent for the airborne molecules. The adsorbing material can be used in air filter systems or as stand-alone adsorbents. Typical applications are selected from but not limited to domestic odour control as well as odour control in cars, warehouses, industry buildings, waste disposal sites, sewage plants and public toilets. The amorphous and anhydrous magnesium carbonate renders its action through adsorbtion of vapors.

One additional aspect of the present invention includes the production and use of the magnesium carbonate of the present invention or composites thereof for air sanitation preventing or treating yeast damage of living spaces and commercial facilities by adsorbing geosmin and dehumidifying air to prevent yeast proliferation.

One additional aspect of the present invention includes the production and use of the magnesium carbonate of the present invention or composites thereof for air sanitation following fire damage.

One additional aspect of the present invention includes the production and use of the magnesium carbonate of the present invention or composites thereof as a fire retardant.

One additional aspect of the present invention includes the production and use of the magnesium carbonate of the present invention or composites thereof as a biomaterial in applications including but not limited to: bone void fillers, depot drug delivery systems and delivery vehicles for local release of therapeutic agents, as well as bone and cartilage repair materials.

One additional aspect of the present invention includes the production and use of the magnesium carbonate of the present invention or composites thereof for collection of toxic waste where the magnesium carbonate of the present invention or composites thereof is used as an adsorbent. In such applications, the material may be spread out over the toxic liquid, which subsequently is adsorbed into the material. After complete adsorption of the toxins, the material can be removed and discarded.

In an additional aspect of the present invention the magnesium carbonate of the present invention or composites thereof are produced and used for collection of oil spill. In such applications, the material may be spread out over the oil and the material adsorbs the oil. After complete adsorption of the oil, the material can be removed and the oil can be retrieved from the material elsewhere.

A further aspect of the present invention includes the production and use of the magnesium carbonate of the present invention or composites thereof in peeling or polishing applications. Non-limited examples of such applications include peeling creams, lotions, solutions and the like for face and body as well as tooth pastes and other dental formulations with polishing properties. In such applications the magnesium carbonate of the present invention may optionally be loaded with a functional agent improving the action of the peeling or polishing application. Non-limiting examples of such agents include flour, whitening agents, vitamins, retinoic acid, trichloroacetic acid, phenol, alpha hydroxy acids like, e.g., glycolic acid, fruit acids like, e.g., citric acid, glycolic acid, lactic acid, malic acid and tartaric acid, beta hydroxy acids like, e.g., salicylic acid.

A further aspect of the present invention includes the production and use of the magnesium carbonate of the present invention or composites thereof is the use of the magnesium carbonate to alter the viscosity and consistency of ink.

BRIEF DESCRIPTION OF THE DRAWINGS

The invention will now be described in detail with reference to the drawing figures, wherein.

DETAILED DESCRIPTION OF THE INVENTION

Figure 1:
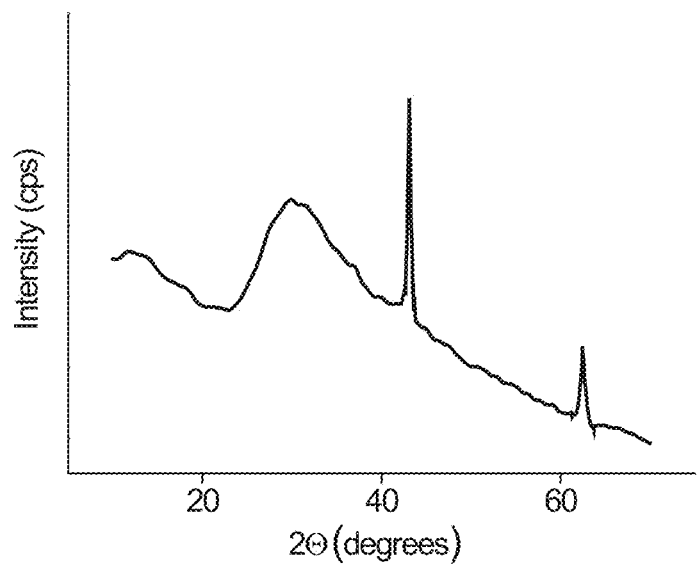
FIG. 1. is a graph illustrating the XRD diffraction pattern for a magnesium carbonate of the present invention, wherein the halo at 2θ~30° indicates the presence of at least one amorphous phase and the sharp peaks belong to crystalline MgO.

The present invention is directed to a novel anhydrous, amorphous, micro porous, high specific surface area magnesium carbonate with extraordinary moisture sorption properties. As is described in detail herein, the material is suitable for use in a wide variety of applications.

The novel anhydrous, amorphous, micro porous, high specific surface area (between 60 and 1500 m²/g) magnesium carbonate according to the invention may be provided as a mixture or composite with other materials, for example for the purpose of tailoring certain properties. As appreciated by the skilled person unavoidable impurities and intermediate products may be present in the final product. The remaining part of the material may be any amorphous or crystalline, organic or inorganic element or compound. Non limiting examples of such other material include salts, like calcium carbonates, crystalline magnesium carbonates, sodium chloride, magnesium nitrate, copper sulfate, hydroxyapatite, strontium acetate, zinc citrate, hydroxides like magnesium hydroxide, strontium hydroxide and silicon hydroxide, oxides like magnesium oxide, iron oxide, silicon dioxide, aluminum oxide, aluminosilicate, metals like gold, silver, zinc, aluminum, as well as organic compounds like cellulose, spider silk and synthetic polymers.

Different suitable methods may be employed, individually or combined, to confirm and quantify the amorphous magnesium carbonate content of the material. These methods can include, but are not limited to, XPS (x-ray photoelectron spectroscopy), Raman spectroscopy, XRD (x-ray diffraction), FTIR (Fourier transform infrared spectroscopy), NMR spectroscopy (nuclear magnetic resonance spectroscopy), ICP-MS (inductively coupled plasma mass spectrometry), EDS (energy-dispersive X-ray spectroscopy), TEM (transmission electron microscopy) ED (electron diffraction) and TGA (Thermogravimetric analysis). As described in Example 1 below, Raman spectroscopy may be employed to reveal the presence of amorphous magnesium carbonate in the material (by the presence of the so called Boson peak at low wavenumbers which is characteristic for amorphous materials, and the distinctive carbonate peak at ~1100 cm$^{-1}$). To confirm the presence and determine the amount of magnesium carbonate in a material, XPS analysis can be employed in the following manner: The magnesium carbonate content in the material can be determined by elemental analysis using XPS, and energy resolved spectrum analysis using the same technique can be used to distinguish between crystalline and amorphous magnesium carbonate: the electron binding energy in the Mg 2 s orbital of amorphous magnesium carbonate is expected to be ~90.7 eV while the binding energy generally is expected to be ~91.5 eV or higher for crystalline magnesium carbonates. The presence of structural water, i.e. hydrated magnesium carbonates, can be elucidated via energy resolved XPS analysis of the O1s peak as described in one of the embodiments below. Other techniques can involve XRD analysis for crystal phase determination of the constituents of a material where the amorphous magnesium carbonate content can be quantified in relation to the crystalline content.

In particular, the presence of amorphous magnesium carbonate can be confirmed by XRD. In an XRD measurement amorphous magnesium carbonate gives rise to either broad halos or just noisy flat signals in the 2θ window between about 10° and 20° as well as between about 25° and 40° when the diffractometer uses CuKα radiation. Example of such halos can be seen in FIG. 1. When the remaining part of a material, consisting of materials other than amorphous magnesium carbonate (including impurities or other elements introduced on purpose), such materials will give rise to peaks in the XRD pattern, as also exemplified in Example 1, and seen in FIG. 1, provided that they are crystalline.

Figure 9:
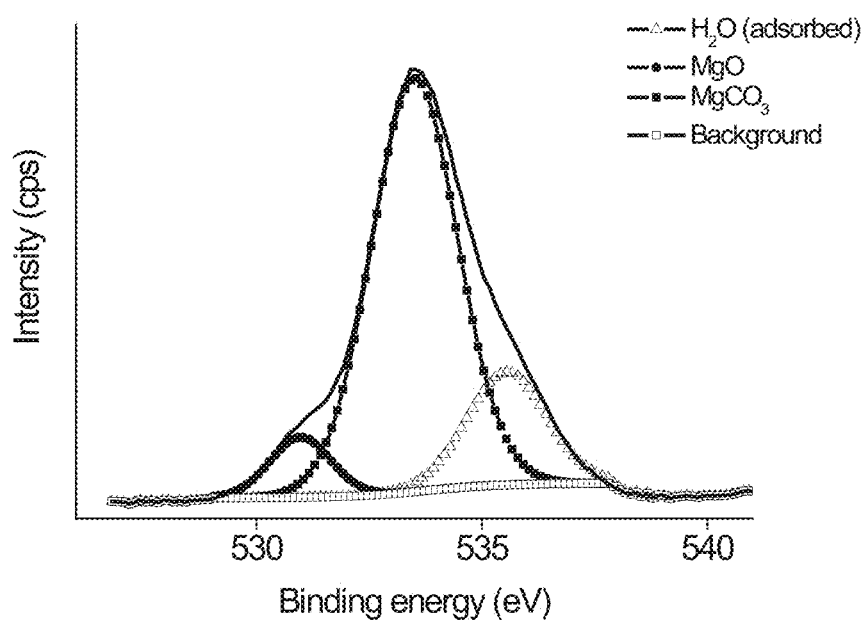
FIG. 9. is a graph illustrating the XPS $O_{1s}$ peak for a magnesium carbonate of the present invention, wherein the peak at 533.5 eV belongs to $MgCO_3$ (solid squares in curve fit), the peak at 531.0 eV belongs to MgO (solid circles in curve fit) and the peak at 535.6 eV belongs to surface adsorbed water (open triangles in curve fit; (the solid lines represent the recorded spectrum; open squares represent the subtracted background.

The amorphous magnesium carbonate according to the present invention is anhydrous. Anhydrous in this respect means that no structural water is associated with the bulk of the material, however water molecules are allowed to be tightly or loosely bound to the surface of the material. In this context, tightly bound water does not imply non-regenerable water (details concerning regenerating moisture sorption ability the amorphous magnesium carbonate of the present invention are described below). Absence of structural water can be verified using X-ray photoelectron spectroscopy (XPS) following sputter cleaning of the surface under vacuum as exemplified in FIG. 9. The lack of structural water in the bulk is verified by energy resolved analysis of the O1s peak: a properly calibrated O1s spectra should contain a peak at ~533.5 eV corresponding to $MgCO_3$, however no peak component corresponding to $H_2O$ or OH-groups should be present in the spectrum other than that for surface adsorbed water which is expected around 535.6 eV.

The magnesium carbonate according to the present invention has a cumulative pore volume of pores with a diameter smaller than 10 nm of at least 0.018 $cm^3/g$, preferably above 0.4 $cm^3/g$, preferably above 0.6 $cm^3/g$ or even more preferably above 0.8 $cm^3/g$, and a cumulative pore volume of pores with a diameter smaller than 10 nm up to 1.5 $cm^3/g$, or more preferably up to 2 $cm^3/g$ or most preferably up to 3 $cm^3/g$ which is illustrated in FIGS. 8, 14, 17, 19, 21, 22, 23, 24 and 25.

The pore size distribution and the cumulative pore volume specified in the above embodiments may be determined by density functional theory (DFT) calculations on the adsorption isotherm with appropriate assumptions about pore shape as exemplified in FIGS. 8, 14, 17, 19, 21, 22, 23, 24 and 25.

Figure 28:
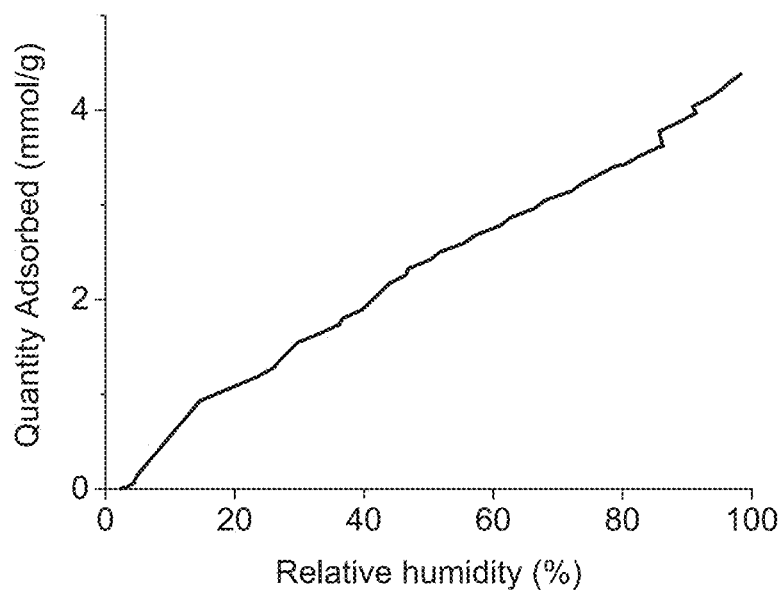
FIG. 28. is a graph illustrating the moisture adsorption of the magnesium carbonate material as prepared in example 15.

The combination of amorphicity and presence of micro pores in the amorphous magnesium carbonate of the present invention, as specified in the above embodiments, is considered to be important for the moisture sorption properties of the material. As is obvious from FIGS. 5 and 16 the amorphous magnesium carbonate of the present invention has a dramatically higher moisture sorption ability at low and intermediate RH as compared to for example the pharmaceutical grade of magnesium carbonate (crystalline hydromagnesite, see FIG. 5) and an amorphous magnesium carbonate that has a volume of pores with a diameter smaller than 10 nm below 0.018 $cm^3/g$, see FIG. 28.

The amorphous magnesium carbonate according to the present invention, features a specific surface area of at least 60 $m^2/g$, preferably of at least 100 $m^2/g$, more preferably of at least 240 $m^2/g$, even more preferably of at least 350 $m^2/g$, most preferably of at least 600 $m^2/g$, and a SSA up to 400 $m^2/g$, preferably up to 800 $m^2/g$, more preferably up to 1000 $m^2/g$, even more preferably up to 1200 $m^2/g$ and most preferably up to 1500 $m^2/g$.

Figure 6:
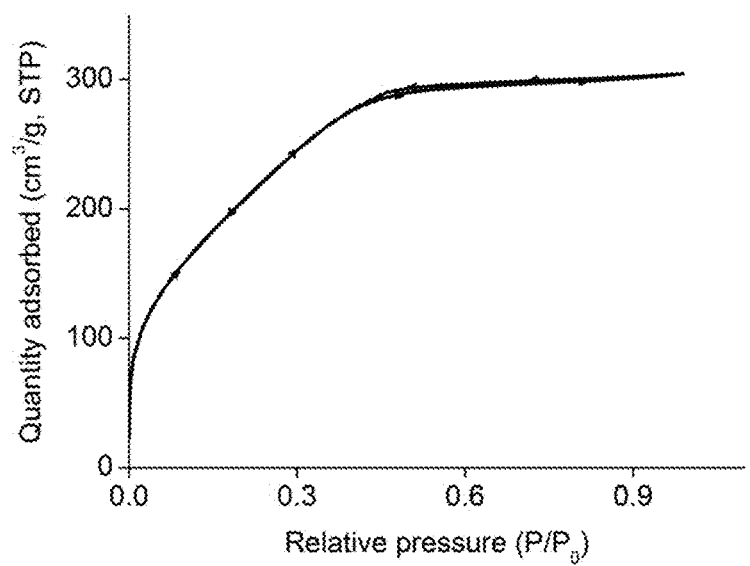
FIG. 6. is a graph illustrating the nitrogen sorption isotherm for a magnesium carbonate of the present invention.
Figure 7:
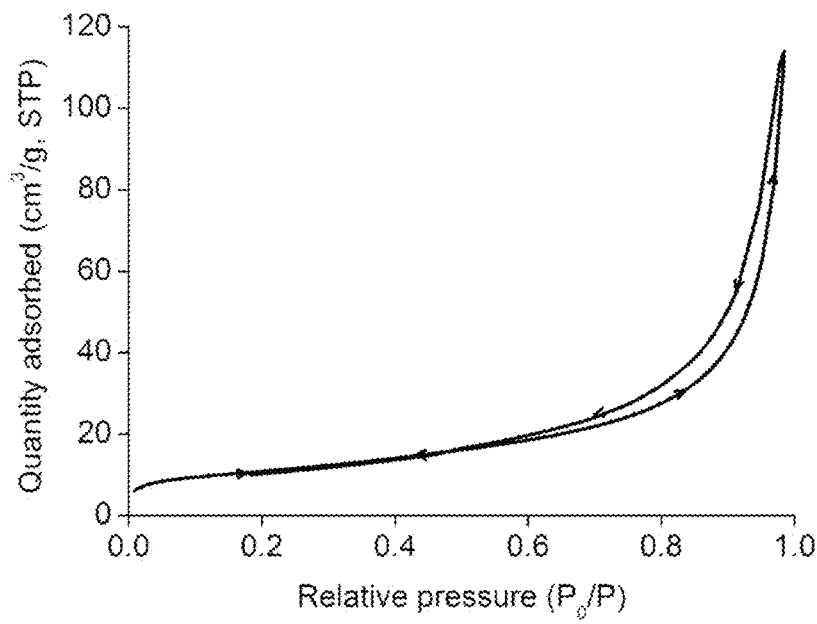
FIG. 7. is a graph illustrating the nitrogen sorption isotherm for hydromagnesite ($Mg_5(CO_3)_4(OH)_2 \cdot 5H_2O$)
Figure 13:
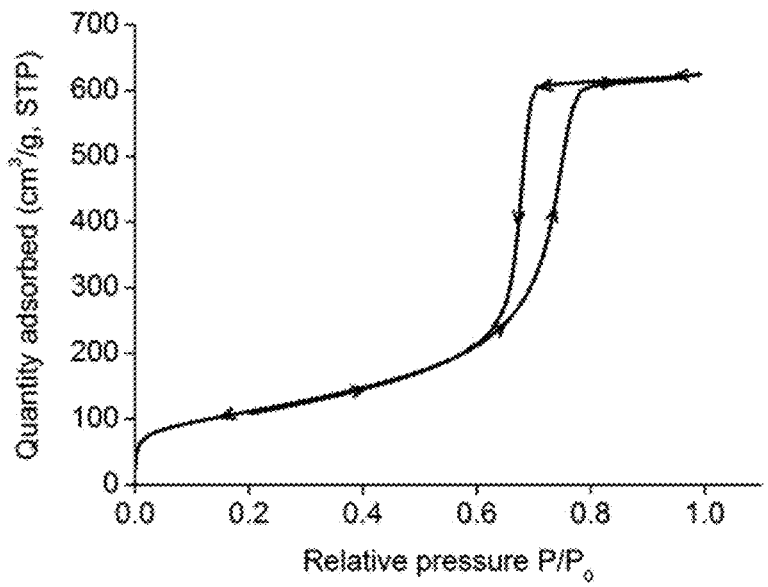
FIG. 13. is a graph illustrating the nitrogen sorption isotherm of a magnesium carbonate of the present invention in which the synthesized powder was heat-treated at 70° C. for 7 days (example 2)

The specific surface area can be determined by employing the BET method to nitrogen adsorption isotherms like those presented in FIGS. 6 and 13. More precisely a multipoint BET analysis is performed on the relative pressure range between 0.05 and 0.3 of the adsorption branch of a nitrogen isotherm performed at boiling nitrogen temperature. If the BET equation does not yield a linear slope in this pressure range, the BET analysis should be employed on a more narrow pressure range for accurate result. The nitrogen adsorption analysis can be performed on an ASAP 2020 from Micromeritics after drying the sample at 70° C. for 2 days. Prior to analysis, the sample tube containing the sample is evacuated with a vacuum set point at 10 µm Hg and heated to at 95° C. for 10 h with a ramping rate of 1° C./min. It should be noted that in the cases when the specific surface area of the amorphous magnesium carbonate of the present invention are of the order of 500 $m^2/g$ or larger it is comparable to that of the exclusive class of high surface area materials such as zeolites, mesoporous silicas, metal organic framework materials, and carbon nanotubes.

A large surface area, i.e. larger than the surface area of a macroscopic solid material, is beneficial for all industrial applications where surface interactions are of importance, including but not limited to drug delivery, catalysis, adsorption of various gases and liquids. It can be appreciated by one skilled in the art that being able to produce an amorphous magnesium carbonate according to the present invention of high surface area will improve the functionality of the material in a range of applications like those mentioned in the summary of invention.

To one skilled in the art it is obvious that the surface area of any material can be increased by diminishing the particle size of said material. A diminished particle size may also increase the amorphicity of a material as measured by XRD. Large surface areas and amorphicity stemming only from such diminishing of the particle size is generally not expected to lead to improved properties in applications of magnesium carbonates in the applications mentioned above and in the examples as well as in other application.

With reference to the above; in one specific embodiment of the present invention the amorphous magnesium carbonate of the present invention with the surface areas detailed above, consists of particles having an equivalent to a sphere diameter of not smaller than 37 nm for more than 1% of their number size distribution.

Another way of assessing the presence of micro pores in the material of the present invention and also assessing a large surface area is by a direct study of nitrogen sorption isotherms. Thus, according to one embodiment of the present invention the amorphous magnesium carbonate of the invention adsorbs more than 20 $cm^3$ nitrogen/g material at STP at a partial nitrogen pressure of 0.5, preferably more than 25 $cm^3$ nitrogen/g material at STP, even more preferably more than 30 $cm^3$ nitrogen/g material at STP, even more preferably more than 50 $cm^3$ nitrogen/g material at STP, even more preferably more than 100 $cm^3$ nitrogen/g material at STP, even more preferably more than 200 $cm^3$ nitrogen/g material at STP, even more preferably more than 250 $cm^3$ nitrogen/g material at STP during a nitrogen adsorption analysis. The nitrogen adsorption ability is confirmed from gas adsorption experiments like those exemplified in FIGS. 6 and 13.

The amorphous magnesium carbonate according to the present invention is stable upon storage for up to 13 weeks or longer. Experiments have shown that the materials can be stable up to 3-5 months and even longer at room temperature and relative humidities above 20%. In some experiments the stability for several months was verified when the material was stored at 30%, 50, 60%, and also in a sealed humidity cabinet with a saturated water vapor atmosphere. The stability of the magnesium carbonate component can be assessed by Differential Thermogravimetic measurements (also commonly denoted as DTA or dTGA measurements in the literature) as exemplified in FIG. 3 and FIG. 4 by observing the peak related to the decomposition of the carbonate at above 350° C. More precisely the analysis is performed with a Thermogravimetric analyzer from Mettler Toledo, model TGA/SDTA851e. Approximately 15 mg of sample is placed in an inert aluminum cup and heated from room temperature to 700° C. under a flow of air where the temperature ramping rate is 10° C./min during analysis. The stability of the material is confirmed by the lack of changes in this peak upon storage in a moisture containing atmosphere and also by the fact that the position of the peak is not shifted noticeably (i.e. more than 10-20° C.) towards lower temperatures. A peak shift towards higher temperatures is however, to be taken as an evidence for stability. Such shifts towards higher temperatures can for example be observed when comparing the experiments performed on a dry amorphous magnesium carbonate according to the present invention, FIG. 3, with those performed on amorphous magnesium carbonate according to the present invention stored for different time periods at saturated water vapor, FIG. 4. For an unstable material, on the other hand, the carbonate decomposition peak at above 350° C. is expected to develop a shoulder and/or split into two or more peaks and also to move towards lower temperatures as is the case e.g. for the magnesium carbonate material described in Botha et al. 2003. The stability of the material of the present invention is industrially favorable when it comes to use in e.g. moist environments and ensures that the material can be transported, stored and also used at high relative humidity at prolonged time periods without, due to structural changes, losing its functional abilities as disclosed in the present invention.

The amorphous magnesium carbonate according to the present invention adsorbs more than 0.3 mmol water/g material at an RH of 1% at 25° C. In some experiments it adsorbs more than 0.8 and even more than 1.5 mmol water/g material. As exemplified in FIG. 5, certain experiments have shown that the material adsorbs even more than 2.4 mmol water/g material at this low relative humidity. The water vapor adsorption ability can be confirmed by first drying the material at 70° C. during at least 48 hours and then performing a water vapor sorption experiment as that exemplified in FIG. 5 and FIG. 16. More specifically this can be performed with an ASAP 2020 from Micromeritics equipped with a water vapor source. Prior to analysis, the sample tube containing the sample is evacuated with a vacuum set point at 10 μm Hg and heated to 95° C. for 10 h with a ramping rate of 1° C./min. The measurement is performed at 25° C. starting at low RH with increasing amounts of water vapor dosed into the sample tube. The amount of moisture adsorbed on the material at a given relative humidity is measured when equilibrium between adsorbed and free water vapor is reached in the sample tube. Equilibrium in this case is defined as follows: equilibrium is reached when the pressure change per equilibrium interval (first derivative) is less than 0.01% of the average pressure during the interval. The time interval is set to 50 sec during the measurement. In one particular aspect of the embodiment the moisture sorption properties of the amorphous magnesium carbonate of the present invention is comparable, or even superior, to those of hydrophilic zeolites, e.g. zeolite Y (600 m$^2$/g, silica/alumina ratio 5.2:1) and also superior to those of commonly used desiccants, e.g. fumed silica (Aerosil) or crystalline hydromagnesite. An example of such a material according to the present invention is given in FIG. 5.

The amorphous magnesium carbonate according to the present invention adsorbs more than 0.5 mmol water/g material at an RH of 2% at 25° C. Experiments have shown that the material adsorbs more than 0.8 or even more than 2.0 mmol water/g material, while other experiments have shown that it adsorbs even more than 3.5 mmol water/g material (see e.g. FIG. 5). The water vapor sorption ability was confirmed as described above.

The amorphous magnesium carbonate according to the present invention adsorbs more than 0.6 mmol water/g material at an RH of 5% at 25° C., and even more than 5.3 mmol water/g material. The water vapor sorption ability was confirmed as described above.

The amorphous magnesium carbonate according to the present invention adsorbs more than 1.0 mmol water/g material at an RH of 10% at 25° C. and even more than 6.3 mmol water/g material. The water vapor sorption ability was confirmed as described above.

The amorphous magnesium carbonate according to the present invention adsorbs more than 1.0 mmol water/g material at an RH of 20% at 25° C. and even more than 8.3 mmol water/g material. The water vapor sorption ability was confirmed as described above.

The amorphous magnesium carbonate according to the present invention adsorbs more than 1.5 mmol water/g material at an RH of 50% at 25° C. and even more than 10.3 mmol water/g material. The water vapor sorption ability was confirmed as described above.

The amorphous magnesium carbonate according to the present invention adsorbs more than 5.0 mmol water/g material at an RH of 90% at 25° C. and even more than 13.5 mmol water/g material. The water vapor sorption ability was confirmed as described above.

Figure 5:
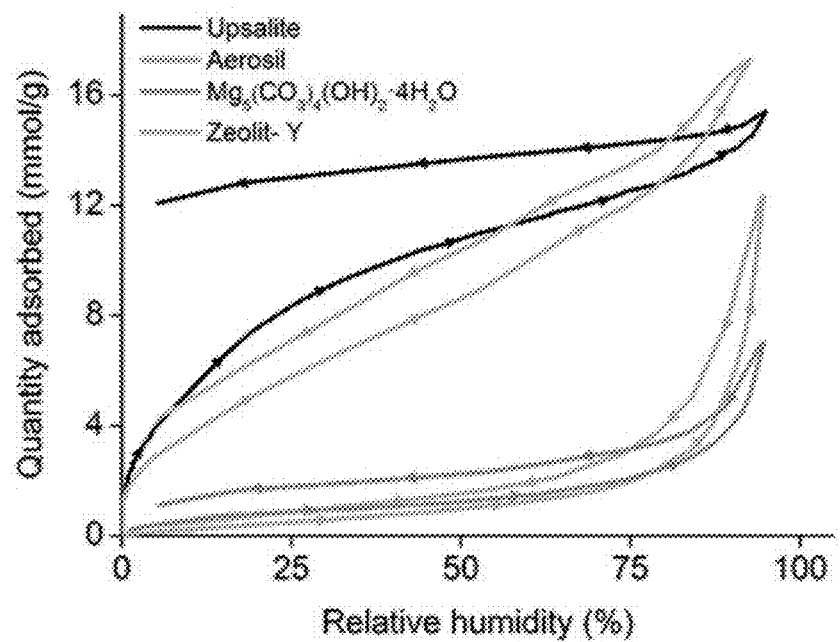
FIG. 5. is a graph illustrating the water sorption isotherms at room temperature for a magnesium carbonate of the present invention (named Upsalite in the figure), $Mg_5(CO_3)_4(OH)_2 \cdot 4H_2O$, Aerosil and Zeolit Y.
Figure 16:
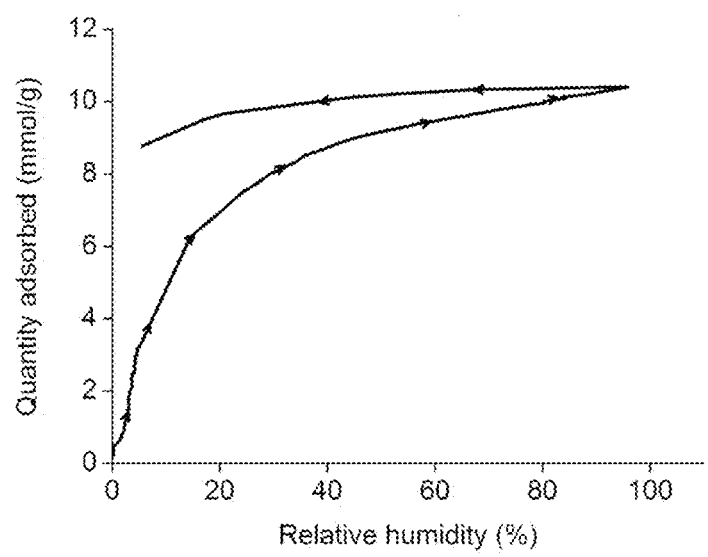
FIG. 16. is a graph illustrating the water sorption isotherm at room temperature for a spray-dried magnesium carbonate of the present invention.

The amorphous magnesium carbonate according to the present invention retains more than 30 wt % of adsorbed moisture when the RH is lowered from 90% to 5% during a water vapor desorption analysis performed at 25° C. as exemplified in FIGS. 5 and 16. Typically the material retains more than 50 wt % or 60 wt % of the adsorbed moisture and even more than 80 wt % of the adsorbed moisture. More precisely the analysis is performed immediately after a water vapor adsorption analysis as described above by lowering the water vapor pressure in the sample tube. The desorption analysis is allowed to start once the RH has reached and equilibrated at at least 94% RH in the sample tube. During the desorption study, the RH in the sample tube is lowered stepwise and the amount of desorbed vapor is measured at specified relative humidities. The amount of water vapor desorbed from the material at a given relative humidity is measured when equilibrium between adsorbed and free water vapor is reached in the sample tube. Equilibrium in this case is defined as follows: equilibrium is reached when the pressure change per equilibrium interval (first derivative) is less than 0.01% of the average pressure during the interval. The time interval is set to 50 sec during the measurement.

The amorphous magnesium carbonate according to the present invention retains more than 40 wt % of adsorbed moisture when the RH is lowered from 90% to 20% during a water vapor desorption analysis performed at 25° C. as exemplified in FIG. 5 and FIG. 16. The water vapor retention ability was confirmed as described above.

The ability to retain moisture in the structure upon lowering of the relative humidity after moisture sorption as described in the above embodiments is a highly favorable property of the material according to the present invention and rather unique amongst moisture adsorbents as exemplified in FIG. 5. As will be appreciated by one skilled in the art, the fact that the material of the present invention not easily lets go of the moisture adsorbed when a lowering of humidity is performed after adsorption prevents moisture from being released to the environment from which it was removed by an accidental or purposeful lowering of the surrounding humidity. As will become clear from below, the fact that only minor energy input is needed to release the moisture adsorbed in the structure to regenerate the moisture sorption properties of the material is an additionally beneficial property of the material of the present invention since it e.g. opens up for energy efficient regeneration of moisture sorption materials.

The moisture sorption properties of the amorphous magnesium carbonate of the present invention can be regenerated after storing the material at RH higher than 90% RH for at least 7 days at room temperature. This can be performed by drying the material at elevated temperatures at 250° C. or more preferably at 150° C., even more preferably at 110° C., or even more preferably at 95° C. or below. A person skilled in the art will be able to determine the time needed to dry the material sufficiently and will find that a longer drying time is needed for low drying temperatures. Applying vacuum to the material during the drying procedure will obviously decrease the time needed for removal of adsorbed water species from the material. When drying, for example, 0.2 g of material at 95° C. under vacuum with a vacuum set point of 10 µm Hg the drying time is typically 5 days or shorter. Experiments have shown that the drying time can be 2 days and even only 20 h or less.

The fact that the moisture sorption properties of the material of the present invention may be regenerated can be confirmed by the fact that at least one of the moisture sorption properties described above is still valid (adsorption properties below 1%, 2%, 5% 10, 20 and 50% RH and/or adsorption properties below 90% RH and/or desorption properties from 90% RH to 5% RH and/or desorption properties from 90% RH to 20% RH).

Theoretical Discussion about the Reaction Mechanism

The amorphous and micro porous magnesium carbonate according to the present invention, $Mg_xCO_y$, wherein x=1-2 and y=3-4, is obtained upon drying of a reaction product between MgO and $CO_2$ (mildly pressurized) in methanol. The $Mg_xCO_y$ material disclosed here is amorphous, and, because it is currently not possible to distinguish between several amorphous compositions of $Mg_xCO_y$, it includes $MgCO_3$, $MgCO_3 \cdot MgO$, and $Mg_2CO_4$, although preferably x=1 and y=3, and any of their combinations as well as their solvates.

For the sake of simplicity, the basic reaction of magnesium carbonate formation from MgO and $CO_2$ in alcohol could be condensed into the following terms:

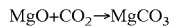

MgO+CO$_2$→MgCO$_3$

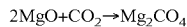

2MgO+CO$_2$→Mg$_2$CO$_4$

However, the reaction between solid MgO and gaseous $CO_2$ does not readily proceed or is too slow, and one skilled in the art will understand that in reality the reaction scheme is much more complex and involves several important intermediates which form in the alcohol phase. By considering the role of these important intermediates, which will be highlighted below, one skilled in the art will also appreciate that the final product, i.e. $Mg_xCO_y$, could be obtained in many ways, i.e. without direct use of MgO, including metallic Mg or several Mg containing inorganic and organic compounds. Therefore, the reaction scheme proposed herein below should not be perceived in limiting terms.

In the old literature, it has often been considered that oxides of alkali and alkaline earth metals in alcohols form oxides with alcohol of crystallization, i.e. MeO·nROH. The modern understanding though suggests that, when dissolved in alcohol, MgO forms alcoholates (also called alcoxides).

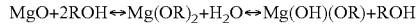

MgO+2ROH⇌Mg(OR)$_2$+H$_2$O⇌Mg(OH)(OR)+ROH

The double-sided arrow above and all other throughout the text should be interpreted as ⇌, i.e. referring to a reversible reaction.

ROH represents an alcohol which can be any kind of alcohol including aliphatic, alkenyl, aromatic, primary, secondary, tertiary alcohol as well as glycol or polyol. Both Mg alcoholate and Mg hydroxyalcoholate could be formed during the course of the reaction. The fact that the reaction proceeds in the indicated order was confirmed by following the isotopic exchange in the CaO—C$_2$H$_5$OH—H$_2$O system.

It has further been discussed in the literature that tertiary systems of alkaline earth metal oxides in alcohol+water can show complex phase diagrams of varying compositions which include not only the Me(OR)$_2$ or Me(OH)(OR).n-ROH, as expected from the reaction above, but also Me(OH)$_2$·nROH. Thus, one skilled in the art will appreciate that $Mg_xCO_y$ disclosed herein could also be obtained from any of the above intermediates by considering the appropriate proportions between the components of the tertiary mixtures as well as availability of water in the system and in situ hydrolysis of then-present compounds and their solvates. FTIR analysis of the samples studied did not reveal the presence of Mg(OH)$_2$·nROH in the system.

During the development of the magnesium carbonate disclosed herein it was found that heating the solution of MgO in alcohol, e.g. 50° C., prior to or during the pressurization with $CO_2$ was beneficial for high yield of MgO-HOCH$_3$, that currently are considered to be an intermediate in the reaction.

Considering that Mg alcoholates could be important intermediates, one skilled in the art will further assert that Mg alcoholates could also be obtained using other chemical routes which could include but are not limited to:

Reaction of metallic Mg with alcohol;
Reaction of Mg(OH)$_2$ with alcohol;
Reaction of Mg amines with alcohol in liquid NH$_3$ as solvent;
Decomposition of Mg hydride, carbide, nitride, amide, sulfide or organometallic compounds containing Mg;
Metatheses of Mg salts with alcoxide of other metals;
Metatheses of alcoxides with alcohols leading to a synthesis of new alcoxides;
Oxidation of alkyl derivatives with oxygen;
Reduction of carbonyl-containing compounds;
Electrochemical reactions in alcohols, e.g. using metallic Mg as the anode or electrolysis of Mg salts.

Alcoxides of metals are very sensitive to moisture, air, and carbon dioxide and behave as "strong base". They can therefore interact both with acids and their anhydrides.

The typical reaction of an alcoxide with acid follows as:

Wherein E=C or S, and X=O or S; and Me=Li, K, Na, Cs, Rb, Mg, Ca, Sr, Ba, Tl.

Upon interaction with $CO_2$, Mg methylate can form Mg dimethylcarbonate.

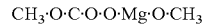

CH$_3$·O·C·O·O·Mg·O·CH$_3$

Mg dimethylcarbonate is similar to Mg hydrocarbonate except that the hydroxyl group is substituted by a metoxy group and thus behaves similarly with respect to acids and water. It should also be mentioned that monomethyl hydroxycarbonate salt of Mg have not been described,

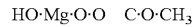

HO·Mg·O·O   C·O·CH$_3$ which would otherwise be expected to exist considering the structure of Mg dimethylcarbonate. Monomethyl hydroxycarbonate of Mg is deemed an important intermediate for producing micro- and/or mesoporous $Mg_xCO_y$ disclosed herein.

Another potentially important intermediate is hemicarbonic acid HOCOOR. The importance of the formation of hemicarbonic acid is highlighted by considering the possibility of the following reaction:

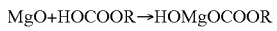

MgO+HOCOOR→HOMgOCOOR

During the development of our material it became clear that pressurizing $CO_2$ gas (1-12 bar) in the reaction vessel containing MgO in alcohol is important, which potentially enables the following reaction:

ROH+$CO_2$↔HOCOOR(Pressure)

The formation of hemicarbonic acid in $CO_2$-alcohol systems has been shown in supercritical fluids at 70-100 bar at 20-40° C. for 2 days by interacting it with diazodiphenylmethane as a probe to catch acid species. These results also showed that in a homologous row of alcohols the rate of hemicarbonic acid formation is the fastest for methanol and the slowest for tert-butanol.

One skilled in the art will also understand that hemicarbonic acid can be produced by interacting monomethylcarbonate with an acid in an organic solvent, e.g. dimethyl ether,

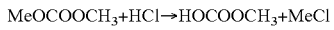

MeOCOOCH$_3$+HCl→HOCOOCH$_3$+MeCl

Thereby, it is also expected that for bivalent Me (e.g. Mg, Ca, Sr, Ba) dimethylcarbonates interacting with water-formed in situ or added in stoichiometric quantities-monomethyl hydroxycarbonic salt and hemicarbonic acid could be obtained although no literature reports on this reaction exist so far.

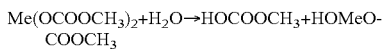

Me(OCOOCH$_3$)$_2$+H$_2$O→HOCOOCH$_3$+HOMeO-COOCH$_3$

Alkylesters of hemicarbonic acid are therefore deemed important intermediates for the formation of $Mg_xCO_y$ disclosed herein.

Orthocarbonic acid, $H_4CO_4$, is another possible important intermediate which has never been isolated either in the form of free acid or its salts but only so far is known to exist in the form of esters, i.e. $C(OR)_4$, or substituted complex ester-salts, e.g. NaCOF$_3$. However, numerous computational models show that salts of orthocarbonic acid can exist. It should be noted that esters of orthocarbonic acid $C(OR)_4$ can be produced from alxocides of Sn, Tl, or Cu. In particular, for monovalent metals Tl, Cu the reaction scheme between alcoxides and carbondisulfide is the following:

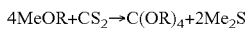

4MeOR+CS$_2$→C(OR)$_4$+2Me$_2$S

Considering the similarity between $CS_2$ and $CO_2$ as acid anhydrides with substituted carbon chalcogenides, the reaction mechanism involving orthocarbonic acid esters $C(OR)_4$ and its salts, i.e. COMe$_4$ (for monovalent metals) and COMe$_2$ (for bivalent metals), is therefore plausible yet it has never been proved. It is also expected that if $CO_2$ were used instead of $CS_2$ the final product should contain some metal oxide in analogy with metal sulfide formed as discussed above.

In all, it infers from above considerations that the mildly pressurized mixture of MgO, $CO_2$, and alcohol represents a rather complex cocktail of different intermediates at equilibrium which can be shifted by changing the concentration, pressure, and temperature of the system. By using FTIR-spectroscopy, the following two intermediates were clearly detectable, viz. MgOHOCH$_3$ and HOMgOCOOCH$_3$.

Therefore, the following chain of reactions, considering the case of methanol, is deemed beneficial for formation of $Mg_xCO_y$ material disclosed herein:

Route 1 (Monomethyl Hydroxycarbonate Route)

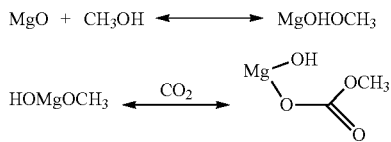

Route 2 (Hemicarbonic Acid Route)

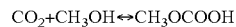

CO$_2$+CH$_3$OH↔CH$_3$OCOOH

MgO+HOCOOCH$_3$↔HOMgOCOOCH$_3$ (as above)

Route 3 (Orthocarbonate Route)

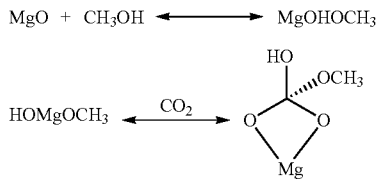

The routes 1, 2, and 3 are non-exclusive and may well occur in parallel under mild $CO_2$ pressure (1-12 bar) and T=20-70° C. One skilled in the art will also understand that if the reaction involving these intermediates is conducted in another solvent than alcohol the suitable temperature range will depend on the boiling and freezing of the said solvent. It is noteworthy that the final product of reactions according to routes 1, 2, and 3, viz.

HOMgOCOOCH$_3$, is a labile substance due to the hydroxyl group present in the vicinity of methoxide group and therefore could produce a solvate of $Mg_xCO_y$ with alcohol of crystallization, i.e. $Mg_xCO_y$·CH$_3$OH. Upon mild heating $Mg_xCO_y$·CH$_3$OH readily releases its alcohol of crystallization and produces a micro- and/or mesoporous powder of $Mg_xCO_y$ as disclosed herein. Some possible reactions involving alcohol of crystallization are shown below:

Final

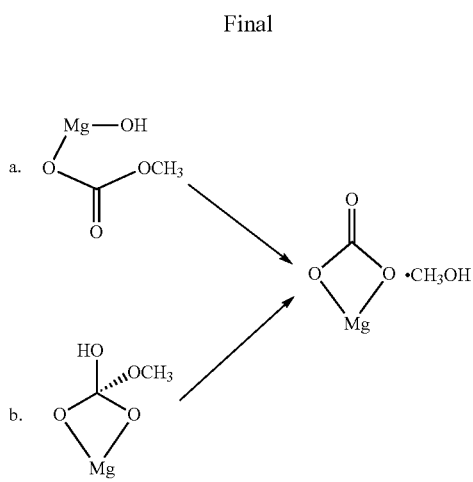

-continued

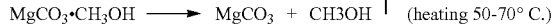

$MgCO_3 \cdot CH_3OH \longrightarrow MgCO_3 + CH3OH \uparrow$ (heating 50-70° C.)

That the product of $Mg_xCO_y \cdot CH_3OH$ drying, e.g. at 70° C., is $Mg_xCO_y$, was verified using FTIR spectroscopy. Obviously, the material can also be heated at higher temperatures as long as it does not decompose but this will be related to unnecessary energy consumption in industrial settings.

Upon visual observation, the degradation goes through several steps since first a gel like consistency is seen which then turns into a white rock, identified as amorphous, anhydrous $Mg_xCO_y$. The mol distribution of the constituent elements, i.e. Mg, C, and O, in the final product suggested that the material can contain any of the following species $MgCO_3$, $MgCO_3*MgO$, and/or $Mg_2CO_4$, which at this point could not be discerned due to the amorphous nature of the product.

Surprisingly, it was observed that the vapors/gases formed during the drying of the liquid phase cannot escape readily through the viscous gel phase and therefore act as templates around which the solidification occurs. These bubbles form the micro and/or mesopores in the produced $Mg_xCO_y$ material and also stand for the extraordinarily high pore volume and surface area of the material disclosed herein. That the gases are trapped in the gel was further exemplified when vacuum (200 mbar) was employed to accelerate the drying at 70° C.: the semisolid phase behaved then as if it was boiling.

Brief synopsis of the mechanism, method, and possible important intermediates includes the following:
Routes 1 (monomethyl hydroxycarbonate route), 2 (hemicarbonic acid route), and 3 (orthocarbonate route) have not been previously shown to lead to formation of $MgOHOCOCH_3$;
$MgOHOCOOCH_3$ could be a labile but important intermediate which could readily produces a solvate of $Mg_xCO_y \cdot CH_3OH$;
$MgOHOCH_3$ and $HOCOOCH_3$ could be other important intermediates for producing $MgOHOCOOCH_3$;
Upon mild heating (50-70° C.) of $Mg_xCO_y \cdot CH_3OH$, produced from $MgOHOCOOCH_3$ in methanol, a micro- and/or mesoporous $Mg_xCO_y$ is formed;
It is currently believed that the evaporating gases, alcohol of crystallization and $CO_2$ gas trapped in the solvent, from the gel phase of $Mg_xCO_y \cdot CH_3OH$ act as templates around which the solidification of $Mg_xCO_y$ occurs;
The reaction of micro- and/or mesoporous $Mg_xCO_y$ formation is facilitated by mildly pressurizing the reaction vessel whereas the mere bubbling of $CO_2$ gas through the reaction medium does not produce the desired product. Under mild pressure conditions a gel phase is formed which is believed to be beneficial for the properties of the final product.
It is further believed to be beneficial to heat the solution of MgO in $CH_3OH$ prior to or during pressurizing at 40-70° C.

The method according to the invention forming the amorphous magnesium carbonate comprises the formation of a liquid or gel, and their subsequent solidification to form a powder or any other solid state mass. Gels may be obtained from the liquids by allowing the liquid to form a gel using any of the following methods, but not limited to, prolonged reaction time, adjustment of the temperature and/or pressure, or changing any other condition obvious for a person skilled in the art that forces the liquid to turn into a gel. The solid magnesium carbonate of the present invention is further obtained by solidification and subsequent drying of the gel or liquid at atmospheric, above-atmospheric or below-atmospheric pressure. Non limiting examples of solidification/drying processes include tray-drying, vacuum drying, spray-drying, freeze-drying, spray-freeze-drying, supercritical drying or any other known industrial or otherwise feasible drying process at temperatures below 350° C., i.e. the temperature of magnesium carbonate decomposition. The solidification and drying of the gel or liquid results in a coarse solid mass that can be ground or similarly transformed into a fine powder.

Experimental

Synthesis of the Liquids:

The amorphous magnesium carbonate according to the present invention are formed starting from opaque or translucent liquids formed in a reaction between one or several magnesium containing compounds (chosen from MgO, $Mg(OH)_2$ and/or any of their respective Mg containing alcoxides chosen from alcohols, having a generic formula of R—OH in which R is any aliphatic or aromatic group, subject to limitations shown in examples below) with pressurized (above atmospheric pressure) carbon dioxide (or any other compound which can serve as the source of it) in an organic solvent, wherein one of the components is preferably but not necessarily alcohol. Non-limiting examples of alcohols include methanol, ethanol, n-propanol, isopropanol, butyl alcohol, pentanol, hexanol, heptanol, octanol, ethylene glycol, glycerine, phenol, or benzoyl alcohol. Optionally, water may form in situ during reaction or may optionally be added to facilitate the reaction in quantities between 0 and 10 vol %. Non limiting examples of additional organic solvent components, which can be both water miscible and immiscible, include acetone, acetonitrile, benzole, chloroform, dichlormethane, diethylether, diisopropylether, dimethylformamide, dioxane, methylester of acetic acid, ethylester of acetic acid, n-hexane, cyclohexane, dimethylsulfoxide, pyridine, tetrahydrofurane, toluol, or xylol. Non-Mg containing compounds may optionally be part of the reaction in quantities not exceeding the weight of the Mg-containing compound. Non limiting examples of such materials include $CaCO_3$, $SrCO_3$, $BaCO_3$, $ZnCO_3$, $Al_2(CO_3)_3$, SrO, BaO, CaO, ZnO, $Zn(OH)_2$, $Sr(OH)_2$, $Ba(OH)_2$, $Ca(OH)_2$, $Al(OH)_3$ and $SiO_2$ and/or any of their respective alcoxides with alcohols having a generic formula of R—OH, wherein R is any aliphatic or aromatic group.

In a further embodiment one type of liquid is formed in a reaction between MgO and carbon dioxide (at above atmospheric pressure) in a reaction medium in which one of the components is an organic solvent, more preferably alcohol.

In one embodiment one type of liquid is formed in a reaction between Mg alcoxide and carbon dioxide at above-atmospheric pressure in which the reaction medium is an organic solvent, which may or may not be water miscible, more preferably alcohol.

In yet another embodiment one type of liquid is formed in a reaction between Mg containing compound and carbon dioxide at above-atmospheric pressure in which the reaction medium is methanol.

In yet another embodiment one type of liquid is formed in a reaction between Mg containing compound and carbon dioxide at above-atmospheric pressure in which the reaction medium is a mixture between alcohol and another organic solvent, which may or may not be water miscible. No limiting example of organic solvent includes acetone, acetonitrile, benzole, chloroform, dichlormethane, diethylether, diisopropylether, dimethylformamide, dioxane, methylester of acetic acid, ethylester of acetic acid, n-hexane, cyclohexane, dimethylsulfoxide, pyridine, tetrahydrofurane, toluol, or xylol.

Synthesis of Gels:

In one embodiment of the invention, gels are formed from the liquid by allowing the liquid to harden into a gel. This can be obtained via methods such as, but not limited to, prolonged reaction time, adjustment of the temperature and/or pressure, or changing any other condition that forces the liquid to turn into a gel.

Synthesis, Solid Material:

One embodiment of the present invention results in a solid material formed by solidification and subsequent drying of the gel or liquid at atmospheric, above-atmospheric or below-atmospheric pressure. Non limiting examples of solidification/drying processes include tray-drying, vacuum drying, spray-drying, freeze-drying, spray-freeze-drying, supercritical drying or any other known industrial or otherwise feasible drying process at temperatures below 350° C., i.e. the temperature of magnesium carbonate decomposition.

One embodiment of the present invention includes one type of powder formed by spray-drying the liquid having set the outlet temperature of the spray-dryer above the boiling point of the organic solvent or the mixture thereof used to produce the liquid, while the inlet temperature is set above the outlet temperature of the spray-dryer.

Synthesis, Film and Coating:

One embodiment of the present invention includes coherent films or coatings formed by solidification and subsequent drying of the gel or liquid applied to a surface at atmospheric, above-atmospheric or below-atmospheric pressure. Non limiting examples of solidification/drying processes include tray-drying, vacuum drying, freeze-drying, spray-freeze-drying, supercritical drying or any other known industrial or otherwise feasible drying process at temperatures below 350° C., i.e. the temperature of Magnesium carbonate decomposition. The solidification and drying of the gel or liquid results in a coherent and solid film or coating.

Synthesis, Dried Powder:

One embodiment of the present invention includes providing dried powder which is formed in any of the ways described above and subsequently heat-treated at temperatures below 350° C. for 10 minutes or longer.

Mixtures:

In one aspect of the invention the amorphous magnesium carbonate is introduced as part of a composite, composition, mixture, formulation or other system (hereafter referred to as a composite) into which the amorphous magnesium carbonate may be incorporated using various methods included, but not limited to, mixing, spray drying, molding, or other feasible method of making a composite. The purpose of introducing the amorphous magnesium carbonate according to the invention in such composite could be any, including, but not limited to improving the functionality or introduction new functionality to a composite in e.g. water sorption processes.

Surface Coatings:

In one embodiment of the invention, the amorphous magnesium carbonate is used in surface coatings alone or as part of a composite as described above. The surface coating can be deposited on any substrate through surface deposition techniques such as, but not limited to, spin coating and electrophoretic deposition. The rationale for using the amorphous magnesium carbonate in a surface coating could be, but is not limited to, to improve and/or add functionality to a product The synthesis of the materials can be divided into three steps as described below:

[Step 1] Mixing a Mg-containing precursor and an alcohol-containing liquid in a reactor, examples of possible ingredients are discussed above. The mixing is preferably performed under stirring and the consistency of the mixture is preferably of liquid character. During this step, the ingredients in the mixture react to form one or several intermediates that later can interact with $CO_2$. The mixture is preferably heated in order to facilitate reactions between the ingredients in the mixture. The reactor can also be pressurized to facilitate reaction between the ingredients or control the boiling temperature of the alcohol-containing liquid. Temperatures between 40° C. and boiling temperature of the liquid are preferable for the reaction to occur, however lower temperatures down to the freezing temperature of the liquid is enough for a less complete reaction. This step typically takes about 3 h to 24 h at 50° C. for liquid volumes of 100 to 3000 ml. Generally, a slightly yellow (transparent to opaque) liquid product is formed during this step. Higher temperatures reduce the time needed for reaction to take place. The $CO_2$ pressure during this step can range from 0.001 to 200 bar above atmospheric pressure, however pressures below 10 bar are preferable.

[Step 2] Reacting the mixture with $CO_2$. In this step, the intermediate products formed during step 1 interact with $CO_2$ to form one or several types of carbonated intermediate products. The reaction is preferably performed under stirring to facilitate reaction. This step can be performed at temperatures ranging from the freezing temperature to the boiling temperature of the liquid, and at $CO_2$ pressures ranging from 0.001 to 200 bar above atmospheric pressure. However, temperatures below 50° C. and pressures below 5 bar are beneficial for carbonation of the intermediate products. During this step, the carbonated intermediate products can form a gel in the reactor, typically this occurs after 4-6 days if the $CO_2$ pressure is 1 bar and the temperature is 20° C. during step 2. Increasing the pressure or adjusting the temperature can result in faster gel formation. However, the gel formation is not crucial for formation of the final magnesium carbonate in step 3. Generally step 2 takes 1-5 days, longer reaction times result in a higher yield of magnesium carbonate in the final material obtained in step 3.

[Step 3] Solidification and drying of the material. In this step, the liquid or gel formed in the reactor during step 2 is dried in order to obtain a solid material. During this step, the carbonated intermediate products formed during step 2 are transformed into anhydrous magnesium carbonate. A solidification of the material is associated with this drying process and the transformation to magnesium carbonate is facilitated when the products from step 2 are dried at temperatures between 60° C. and 300° C. However, the transformation to magnesium carbonate also occurs at lower temperatures but can take up to several weeks if the drying is performed at room temperature. Depending on the intermediates formed during step 1 and 2, presence of water during step 3 could facilitate the transformation to magnesium carbonate via hydrolysis. After complete transformation of the intermediate products formed in step 2 to magnesium carbonate, traces of unreacted Mg-containing precursor material can reside in the final product. Careful considerations regarding the conditions during step 1 and 2 can minimize the amount of unreacted precursor material in the final product. The drying and solidification process in step 3 can include techniques such as spray drying or oven drying.

Specific Example

In a preferred embodiment of the invention MgO is used as the Mg-precursor and methanol ($CH_3OH$) as the alcohol and the steps of the method comprise:

[Step 1] Mixing a Mg-containing precursor and an alcohol-containing liquid:

MgO (e.g. 4 g) and methanol ($CH_3OH$) (e.g. 60 ml) are mixed, the suspension is heated to between 50° C. and 70° C. for 3-4 hours to form the intermediate $Mg(OH)(OCH_3)$, most preferably to 50° C. The solution is continuously stirred during this step.

[Step 2] Reacting the mixture with $CO_2$:

The solution, now containing $Mg(OH)(OCH_3)$, is pressurized with 1-3 bar above atmospheric pressure $CO_2$ to form the intermediate $Mg(OCO)(OCH_3)_2$ and/or $Mg(OCO)(OCH_3)(OH)$. The $CO_2$ pressure can be applied during step 1 as well, i.e. when MgO and methanol is mixed. At this point the temperature is between room temperature (i.e. 25° C.) and up to about 55° C. The solution is continuously stirred during this step. Higher temperatures decreases the solubility of $CO_2$ in the liquid, which is negative for the reaction since $CO_2$ is needed not only to form the intermediates described above, but also since extra $CO_2$ will dissolve in the liquid and physically bond to the same intermediates. $CO_2$ dissolved in the liquid and $CO_2$ physically bonded to the $Mg(OCO)(OCH_3)_2$ and/or $Mg(OCO)(OCH_3)(OH)$ is responsible for the formation of the micropores in the material when it is released as gas upon depressurization of the reaction vessel and then causes an expansion of the material. Hence, pressure and an excess of $CO_2$ is needed during this step for the later formation of pores in material, i.e. for a complete transformation of MgO to $MgCO_3$ and also formation of micropores, the $CO_2$:MgO molar ratio needs to be higher than 1:1. This reaction step where $Mg(OCO)(OCH_3)_2$ and/or $Mg(OCO)(OCH_3)(OH)$ is formed continues for approximately 2-4 days. A higher temperature and pressure leads to a faster gel formation but also to a less complete reaction.

A) Depressurizing:

After 3-4 days the reaction vessel is depressurized, the depressurization is done fast, i.e., within minutes. It is at this point the micropores in the material are formed when the dissolved and physically bound $CO_2$ is released as described above. To allow the liquid/gel to expand upon release of $CO_2$, the pressure of the $CO_2$ gas is reduced to atmospheric pressure, i.e. from 1 to 0 bar above atmospheric pressure, in the reactor and at the same time the temperature is increased to 70-100° C. in order to decrease the solubility of the $CO_2$ in the liquid/gel and to solidify the material. If the material is in the form of a liquid at this point it turns into a gel in a matter of minutes when the temperature is raised and the solution is depressurized. A visible swelling of the gel can be observed at this time before the material solidifies completely. At this point, a temperature at or above 70° C. is recommended in order to solidify the material rapidly since this will conserve the micropores in the material, a low temperature at this stage will produce a material with a lesser amount of micropores.

B) Drying:

To dry the material a furnace, rotary evaporator or other drying equipment can be used. During the drying of the material the mean pore size increases a bit (from approximately 3 nm up to about 7 nm). When the material is being dried the organic groups that remains in the material from the synthesis are being released which is what causes the pore size increase. For a complete removal of the organic groups (i.e. a "pure" material) drying above 250° C. is needed, the purity of the material is increased with the drying temperature.

To analyze the material synthesised in the specific example the following methods and equipment may preferably be used:

Nitrogen sorption measurements can be carried out at 77 K using an ASAP 2020 from Micromeritics. The samples are degassed at 95° C. under vacuum for 10 h prior to analysis with a vacuum set point of 10 μm Hg. The specific surface area (SSA) are determined by applying the 5 point Brunauer-Emmet-Teller (BET) equation (Brunauer S, Emmet P H, Teller E, J Am Chem Soc, 1938, 60:309) to the relative pressure range 0.05-0.30 of the adsorption branch of the isotherm. The pore size distribution are determined using the DFT method carried out with the DFT Plus software from Micrometrics using the model for nitrogen adsorption at 77 K for slit-shape geometry with no-negative regularization and high smoothing ($\lambda$=0.02000).

X-ray diffraction (XRD) analysis can be performed with a Bruker D8 TwinTwin instrument using Cu-$K_\alpha$ radiation. Samples are ground and put on a silicon zero background sample holder prior to analysis. The instrument are set to operate at 45 kV and 40 mA. Analyses of the diffractogram can be performed using the software EVA V2.0 from Bruker.

Infrared spectroscopy (FTIR) can be performed with a Bruker Tensor27 instrument using a Platinum ATR diamond cell. A background scan are recorded prior to the measurement and subtracted from the sample spectrum, 32 scans are signal-averaged for each spectrum.

Figure 30:
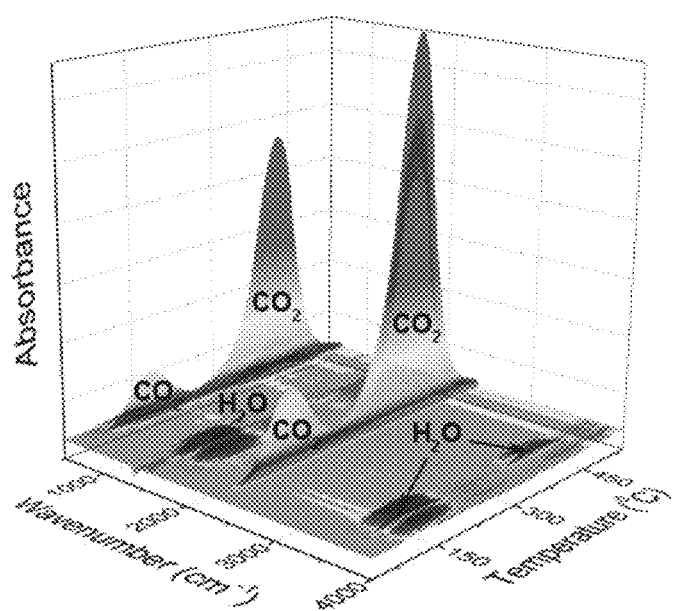
FIG. 30. is a graph illustrating the EGA data for a representative sample of the magnesium carbonate according to the invention.
Figure 31:
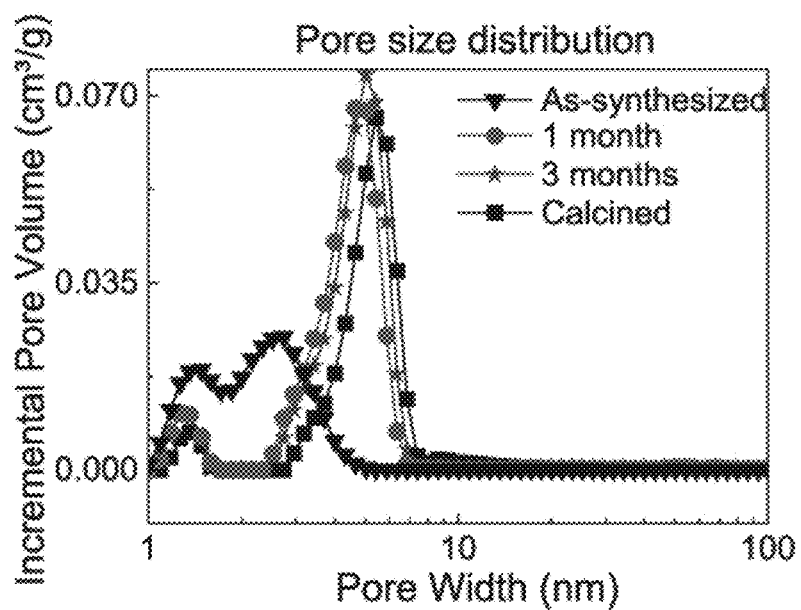
FIG. 31. is a graph illustrating the growth in pore size associated with decomposition of organic groups and evolution of $H_2O$, $CO_2$ and $H_2$ from the magnesium carbonate according to the invention.

The effects of drying at an elevated temperature is shown in FIG. 30 where the Evolved gas evolution (EGA) data from a representative sample of the magnesium carbonate according to the invention is shown. EGA detects the decomposition products from a material, and in FIG. 30 it can be seen that between 100-250° C. $CO_2$ and $H_2O$ is detected. This is due to remaining —OH and —$OCH_3$ groups in the material, above 250° C. the carbonate decomposes which can be seen by the massive formation of $CO_2$ above this temperature. FIG. 31 shows the growth in pore size at different time points for a material stored at 70° C. and also calcined at 300° C., associated with decomposition of the organic groups. The pore size distribution for the as-synthesised material (triangle), which is the material directly after step 3B above that has been dried at 70° C., the same material stored for 1 (circle) and 3 (star) months at 70° C. and the same material that has been calcined (square), i.e. dried at 300° C., are shown. Table 1 displays the pore volume and surface areas associated with the increased pore size due to decomposition of the organic groups.

TABLE 1

Representative values for specific surface area (SSA), pore volume and mean pore widths for the material after different storage conditions, as measured using nitrogen sorption

| Sample | As-synthesized | 1 month 70° C. air | 3 months 70° C. air | Calcined 300° C. $N_2$ |
|---|---|---|---|---|
| SSA $[m^2/g]^a$ | 638 ± 5 | 397 ± 3 | 387 ± 2 | 265 ± 1 |
| Total pore volume $[cm^3/g]^b$ | 0.36 | 0.50 | 0.51 | 0.42 |
| DFT Pore width $[nm]^c$ | 2.5 | 4.7 | 5.0 | 5.5 |
| Limiting micropore volume $[cm^3/g]^d$ | 0.21 ± 0.00 | 0.13 ± 0.00 | 0.13 ± 0.00 | 0.10 ± 0.00 |

$^a$Established with the BET equation, using 5 points in the relative pressure range from 0.05 to 0.3
$^b$Single point adsorption at $P/P_0 \approx 1$
$^c$Established by DFT analysis of the nitrogen adsorption isotherm
$^d$According to the D-A equation, the divergence for all the values are less than 0.001

The understood reaction mechanisms in the preferred embodiment as described above are:

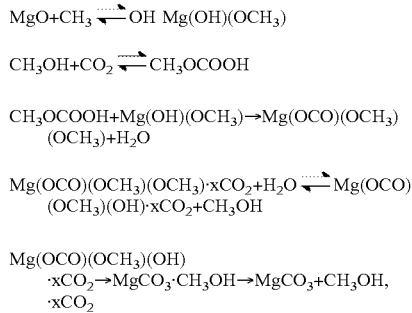

$$MgO + CH_3OH \rightleftharpoons Mg(OH)(OCH_3)$$

$$CH_3OH + CO_2 \rightleftharpoons CH_3OCOOH$$

$$CH_3OCOOH + Mg(OH)(OCH_3) \rightarrow Mg(OCO)(OCH_3)(OCH_3) + H_2O$$

$$Mg(OCO)(OCH_3)(OCH_3) \cdot xCO_2 + H_2O \rightleftharpoons Mg(OCO)(OCH_3)(OH) \cdot xCO_2 + CH_3OH$$

$$Mg(OCO)(OCH_3)(OH) \cdot xCO_2 \rightarrow MgCO_3 \cdot CH_3OH \rightarrow MgCO_3 + CH_3OH, \cdot xCO_2$$

In another laboratory experiment the amorphous magnesium carbonate according to the invention is formed in a reaction between 120 ml methanol and 8 g MgO in a $CO_2$ atmosphere, leading to the formation of a gel, and subsequent solidification and drying of the obtained product. The initial temperature in the reaction vessel containing methanol and MgO is set to 50° C. and the $CO_2$ pressure is set to 3 bar (above atmospheric pressure). After 4 h, the temperature is lowered to 25° C. and the pressure is lowered to 1 bar (above atmospheric pressure) in the reaction vessel. After a couple of hours of reaction, the initially milky white suspension turns into an opaque or translucent yellowish liquid. After about 4 days, a gel formation occurs in the reaction vessel and the reaction is deliberately terminated by a gentle depressurization of the reaction vessel. The gel is subsequently transferred onto a tray and dried in an oven set to 70° C. which leads to a solidification and drying of the gel. In this particular case, the solidification process takes less than 1 h while the drying process takes several days. After being dried, the solidified material is ground to a powder, using e.g. ball milling. It is obvious that one skilled in the art can choose from several available grinding processes such as mortar, impact, attrition, jet grinding or any other industrially suitable type. Alternatively the powder is heat-treated after the solidification and drying as described above prior to the grinding. After drying above 250° C. the powder obtained a surface area of 240 $m^2/g$ and a total pore volume of 0.42 $cm^3/g$.

In further experiments the amorphous magnesium carbonate according to the invention is formed in a reaction between 120 ml methanol and 8 g MgO in a $CO_2$ atmosphere, leading to formation of a liquid and subsequent solidification and drying of the obtained product. The initial temperature in the reaction vessel methanol and MgO is set to 50° C. and the $CO_2$ pressure is set to 3 bar (above atmospheric pressure). After 4 h, the temperature is lowered to 25° C. and the pressure is lowered to 1 bar (above atmospheric pressure) in the reaction vessel. After a couple of hours of reaction, the initially milky white suspension turns into a slightly yellow liquid. After 2 days, the reaction is deliberately terminated by a gentle depressurization of the reaction vessel. The liquid is subsequently transferred to a tray and dried in an oven set to 70° C. which leads to a solidification and drying of the liquid. In this particular case, the solidification process takes less than 1 h while the drying process takes several days. After being dried, the solidified material is ground to a powder, using e.g. ball milling. It is obvious that one skilled in the art can choose from several available grinding processing such as mortar, impact, attrition, jet grinding or any other industrially suitable type. Alternatively the powder is heat-treated after the solidification and drying as described above prior to the grinding.

Currently preferred materials to start the reaction of forming the amorphous magnesium carbonate include MgO, $CO_2$ and an alcohol, such as e.g. methanol.

Two aspects of the method of synthesizing the amorphous magnesium carbonate according to the invention deserve further discussion. If $CO_2$ is merely passed (bubbled) through a methanolic suspension of MgO or another magnesium containing material at atmospheric pressure, no reaction is observed. During the development of the particular amorphous magnesium carbonate materials, we surprisingly found that moderately pressurized $CO_2$ gas (preferentially ~1-3 bar above atmospheric pressure or higher) in a sealed container saturated with $CO_2$ converts MgO to anhydrous magnesium carbonate in methanol. Nothing in the previous art has suggested that (a) anhydrous magnesium carbonate can be produced in alcoholic suspensions and (b) that moderate pressure will be most favorable to produce the desired effect. On the contrary, earlier teachings suggested that Magnesium carbonate cannot be obtained from methanolic suspensions, unlike the carbonates of Ca, Ba and Sr. We have also further observed that $CO_2$ pressure in the reaction vessel has a drastic impact on the gelation time, which is decreased threefold when the pressure is kept at 3 bar over atmospheric pressure throughout the reaction. We have also observed that the excessive pressure may also result in a lower yield of magnesium carbonate in the final product and produce more traces of unreacted MgO.

EXAMPLES

Example 1

| | |
|---|---|
| MgO | 8 g |
| Methanol | 120 ml |
| $CO_2$ (gas) | 3 & 1 bar (above atmospheric pressure) |

8 g MgO powder was placed in a glass bottle together with 120 ml methanol and a stirring magnet. The solution was put under 3 bar above atmospheric pressure $CO_2$ pressure and heated to 50° C. After approximately 3 hours the mixture was allowed to cool to room temperature and the $CO_2$ pressure was lowered to 1 bar above atmospheric pressure. The initially milky white suspension in the reaction vessel transformed gradually into a slightly yellowish liquid in the reaction vessel after a couple of hours. The reaction continued for about 4 days until a gel had formed in the reaction vessel. Subsequently the pressure in the reaction vessel was brought to atmospheric pressure and the gel was collected and put onto a tray for drying in an oven at 70° C. The latter caused the gel to solidify within an hour. The solidified material was left in the oven to dry for 2 days.

Material Characterization, Example 1

The dried material formed a coarse powder that was primarily amorphous with traces of unreacted and crystalline MgO, see X-Ray Diffraction (XRD) pattern in FIG. 1. The sharp peaks at 43° and 62° 2θ originate from the unreacted MgO while the halo peak between 25° and 40° 2θ is indicative of at least one amorphous phase.

Figure 2:
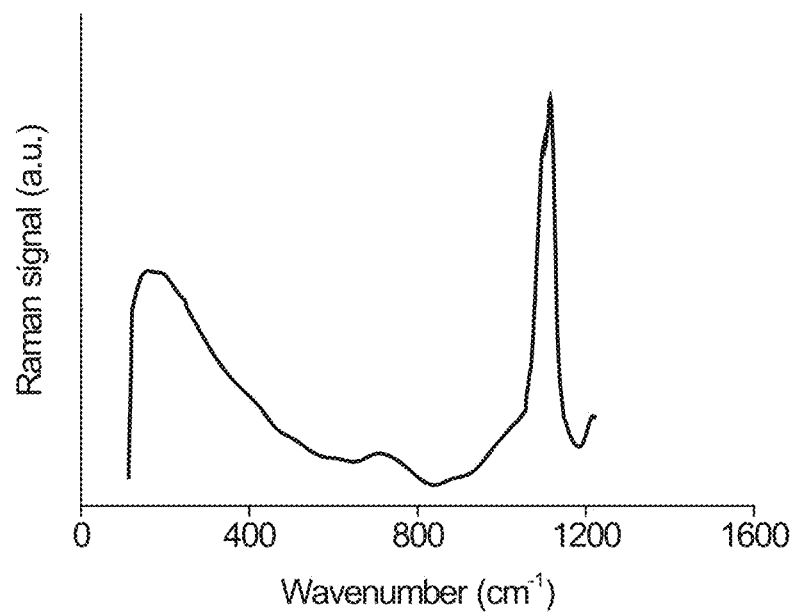
FIG. 2. is a graph illustrating the Raman spectrum for a magnesium carbonate of the present invention, wherein the peak at ~1100 cm$^{-1}$ is from the carbonate group and the broad halo with centrum at 100 cm$^{-1}$ is a Boson peak.

Raman spectroscopy reveals that the powder is indeed composed of magnesium carbonate, see FIG. 2, where the band at ~1100 cm$^{-1}$ corresponds to vibration of the carbonate group. Moreover, a broad halo, or the so-called Boson peak, with a maximum at ~100 cm$^{-1}$ further witnesses of the amorphous character of the powder.

Figure 10:
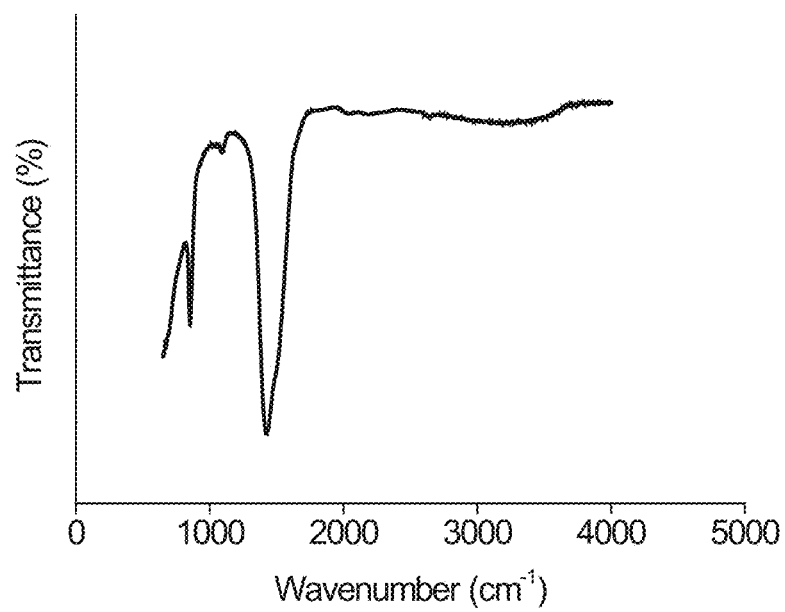
FIG. 10. is a graph illustrating the FTIR spectrum for a magnesium carbonate of the present invention, wherein the three visible bands (1440 cm$^{-1}$, 1100 cm$^{-1}$ and 650 cm$^{-1}$) are all due vibrations of the carbonate group.

When examined with Fourier transform infrared spectroscopy (FTIR), see FIG. 10, the material shows absorption bands at ~1440 cm$^{-1}$, ~1100 cm$^{-1}$ and ~850 cm$^{-1}$ which all correspond to the carbonate group. No water of crystallization is visible in this spectrum.

Figure 3:
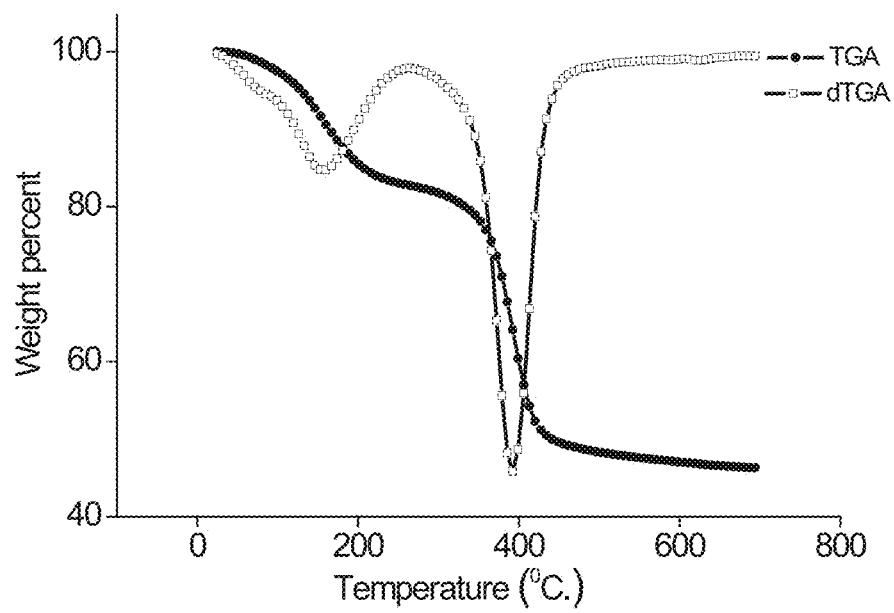
FIG. 3. is a graph illustrating the TGA and dTGA/DTA curves for a magnesium carbonate of the present invention, illustrating how the decomposition at 390° C. pertains to $MgCO_3$ and the decomposition prior to that (i.e. observed at lower temperatures) is due to the loss of remaining organic groups.
Figure 4:
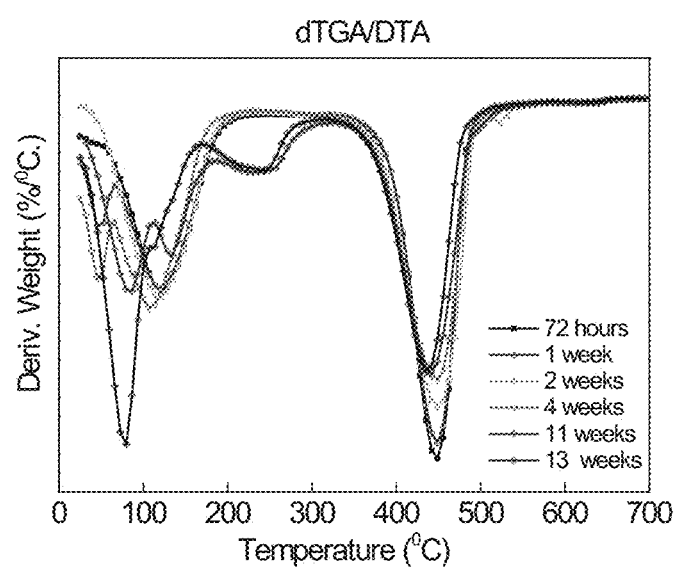
FIG. 4. is a graph illustrating the dTGA curves for a magnesium carbonate of the present invention, wherein the sample has been stored at 100% humidity and room temperature for the displayed time periods and no visible change in the peak position for the peak at approximately 440° C. can be seen.
Figure 11:
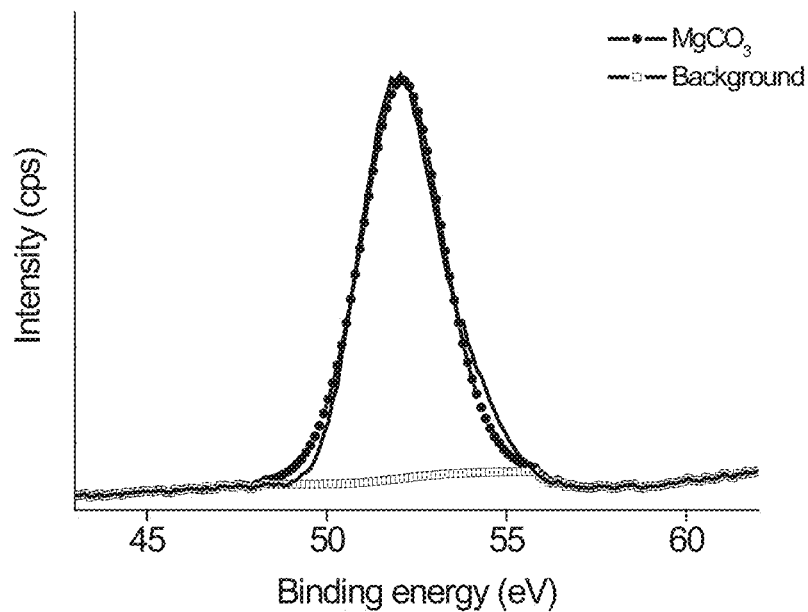
FIG. 11. is a graph illustrating the XPS $Mg_{2p}$ peak for a magnesium carbonate of the present invention, wherein the peak at 52.1 eV belongs to $MgCO_3$ (solid circles in curve fit) and the solid line represents the recorded spectrum and the open squares represent the subtracted background.

The anhydrous character of the bulk material is further confirmed by Thermal Gravimetric Analysis (TGA), see FIG. 3, where the loss with a maximum at 150° C. is due to loss of remaining organic groups. X-ray photoelectron spectroscopy (XPS) confirms the anhydrous nature of the magnesium carbonate: Energy resolved spectra were recorded for the $Mg_{2p}$ and $O_{1s}$ peaks, see FIGS. 9 and 11. The position of the $Mg_{2p}$ peak at 52.1 eV and $O_{1s}$ peak at 533.5 eV are indicative of magnesium carbonate, and the $O_{1s}$ peak does not contain any components for crystal water, which otherwise would have appeared at 533-533.5 eV. The shoulder seen at 535.6 eV is located between the binding energies for liquid water (539 eV) and ice (533 eV) and hence is representative for surface adsorbed water as previously described for surface adsorbed water on carbon fibers. The shoulder seen at 531.0 eV shows the presence of MgO in the powder. No presence of $Mg(OH)_2$ was observed in the bulk which, expectedly, would have resulted in a peak at 532.4 eV.

In order to analyze the pore structure and water sorption capacity of the produced amorphous magnesium carbonate according to the present invention, $N_2$ and $H_2O$ vapor sorption analyses were carried out. FIG. 6 shows the $N_2$ sorption isotherm for the magnesium carbonate according to the present invention and displays a typical Type 1 shape of the isotherm according to the IUPAC classification, which is indicative of a microporous adsorbent. The lack of hysteresis between the adsorption and desorption branches in the $N_2$ isotherm is a distinct feature for microporous. FIG. 5 shows the isotherm for $H_2O$ vapor adsorbed on the magnesium carbonate according to the present invention, which provides information about the materials interaction with water molecules.

Based on the massive $H_2O$ vapor adsorption at low RHs, it is evident that the produced amorphous magnesium carbonate material, according to the present invention, strongly interacts with water molecules and shows a strong hydrophilic behavior. The limited amount of desorption from the material when the RH is reduced from ~95% to ~5% is further proof of the strong interaction between water molecules and the amorphous magnesium carbonate according to the present invention. It should, however, be noted that no signs of hydrate formation of the material is seen using XRD after the isotherm is completed and that the isotherm can be repeated with similar result after heat treatment of the magnesium carbonate according to the present invention at moderate temperature (95° C.).

Both isotherms were analyzed further to establish both the specific surface area (SSA) of the material according to the Brunauer-Emmet-Teller (BET) equation, and the microporous properties according to the Dubinin-Astakhov (D-A) model, see Table 2.

It should be noted that the total pore volume given in Table 2 refers to the total volume of pores filled with nitrogen gas at saturation pressure in a nitrogen sorption experiment carried out at 77 K. This is also the pore volume referred to elsewhere in the text when a pore volume is given without reference to a specific pore size interval.

The hydrophilic nature of the material was further reflected in the greater characteristic energy for adsorption of $H_2O$ compared to $N_2$. The discrepancy in limiting micropore volume ($w_0$) —in which the value obtained from the $N_2$ isotherm is that normally reported in the literature—and modal equivalent pore size obtained from the two isotherms is most likely due to site-specific interaction between the $H_2O$ species and the material, not only in the micro-pores but also on the exterior of the material and in pores larger than 2 nm.

The SSA of the amorphous magnesium carbonate powder according to the present invention is observed to be ~800 m$^2$/g which is up to two orders of magnitude larger than corresponding values reported for any other form of magnesium carbonate, with commercial (crystalline) analogues typically having SSAs of about 4-18 m$^2$ g$^{-1}$. For previously reported amorphous magnesium carbonate produced by thermal decomposition of hydrated magnesium carbonate forms, the highest SSA found in the literature is ~50 m$^2$ g$^{-1}$. In fact, the SSA observed for the amorphous magnesium carbonate according to the present inventions is extraordinarily high, not only for magnesium carbonate, but also for alkaline earth carbonates and minerals in general. This places the amorphous magnesium carbonate according to the present invention in the exclusive class of high surface area nanomaterials including meso-porous silica, zeolites, metal organic frameworks (MOFs), and carbon nanotubes.

TABLE 2

Structural and chemical characteristics of the amorphous magnesium carbonate according to the present invention obtained from $N_2$ and $H_2O$ vapor isotherms.

| Adsorbate | $N_2$ | $H_2O$ |
|---|---|---|
| SSA[1] (m$^2$/g) | 800 ± 3.60 | — |
| Total pore volume (cm$^3$/g) | 0.47 | — |
| $w_0$, limiting micropore volume[3] (cm$^3$/g) | 0.28 ± 0.000559 | 0.16 ± 0.0102 |
| Equivalent surface area in micropores[3] (m$^2$/g) | 549 | 478 |
| Characteristic energy of adsorption[3] (kJ/mol) | 11.4 | 41.0 |
| Modal equivalent pore width[3] (nm) | 1.75 | 1.09 |
| Correlation coefficient of fit[3] | 0.999 | 0.977 |

Figure 8:
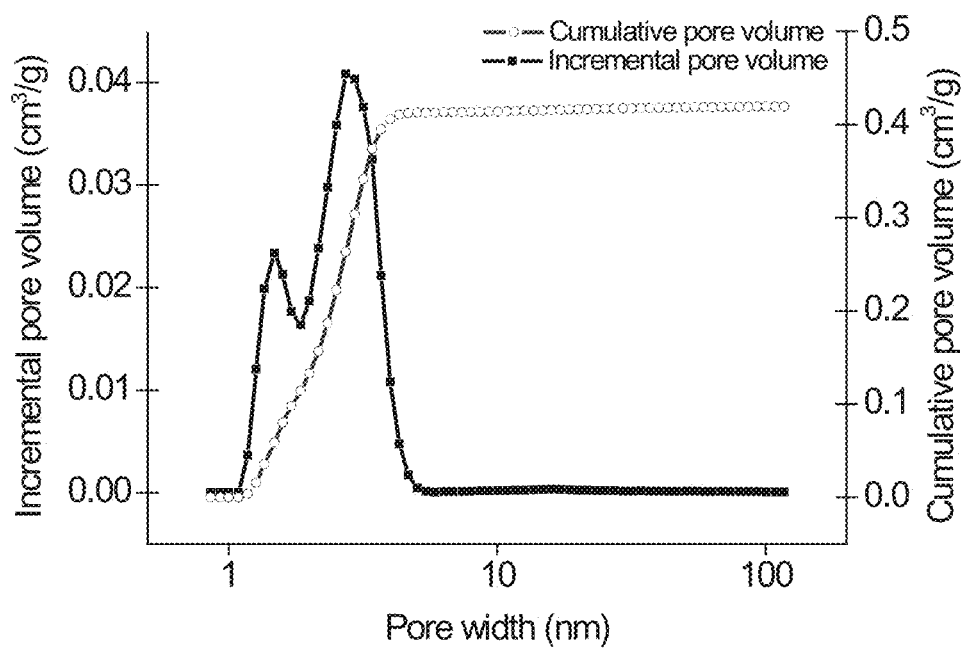
FIG. 8. is a graph illustrating the DFT-based pore size distribution for a magnesium carbonate of the present invention, wherein the pore size distribution has a maximum around 3 nm and the cumulative pore size distribution gives that 98% of the pore volume is constituted of pores with a diameter smaller than 6 nm.
Figure 12:
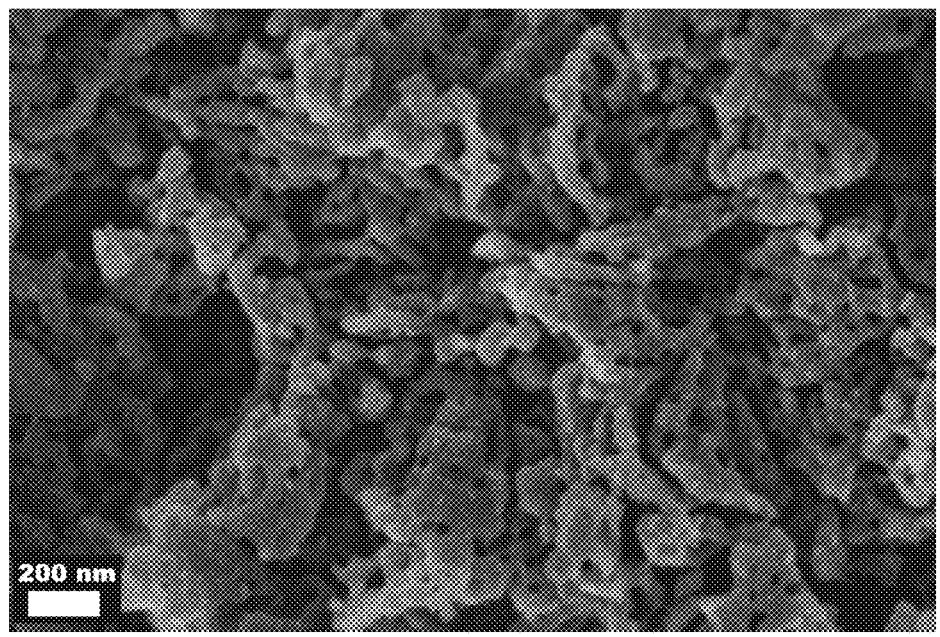
FIG. 12. is a SEM image of a magnesium carbonate of the present invention.

[1]According to the 5-point BET equation applied in the relative pressure range from 0.05 to 0.3
[2]Single point adsorption at P/P0 ≈ 1
[3]According to the Dubinin-Astakhov equation The pore size distribution (see FIG. 8) of the sample was evaluated using the DFT Plus software from Micromeritcs using the model for nitrogen at 77 K on carbon with slit-shaped pores. The DFT-based cumulative pore size distribution gives that about 98% of the pore volume is constituted by pores with a diameter smaller than 6 nm while the remaining pore volume is made up of pores with a broad size distribution between 8 and 80 nm centered around 16 nm. As can be seen in FIG. 8 the cumulative pore volume of pores with a diameter smaller than 10 nm is above 0.40 cm$^3$/g. When examined with scanning electron microscopy (SEM), these larger pores are clearly visible in some parts of the material as illustrated in FIG. 12. These larger pores are, however, not visible throughout the entire material, which is consistent with the limited contribution to the total pore volume from such pores.

The water sorption capacity of the material is interesting from an industrial and technological point of view and it is, hence, compared to three commercially available desiccants, viz. fumed silica (SSA: 196 m$^2$ g$^{-1}$), hydromagnesite (SSA: 38 m$^2$ g$^{-1}$) and the micro-porous Zeolite Y (SSA: 600 m$^2$ g$^{-1}$, silica/alumina ratio 5.2:1), see FIG. 5. The H$_2$O vapor adsorption isotherm for the amorphous magnesium carbonate according to the present invention displays similarities with the hydrophilic zeolite at very low RHs (<1%) and shows on an even higher adsorption capacity for the amorphous magnesium carbonate according to the present invention compared to the zeolite at RHs between 1 and 60%. This behaviour contrasts largely to that of the other two non-porous materials that mainly adsorb H$_2$O at RH >60%. The H$_2$O vapor adsorption behavior for the amorphous magnesium carbonate according to the present invention was also studied by dynamic vapor sorption (DVS) which confirmed that the material has an extraordinary capacity to adsorb H$_2$O vapor, even at extremely low RH, a property highly desirable for desiccants in various applications. Heating the sample to 95° C. appeared to regenerate the water sorption capacity without any crystal phase changes.

The characterization described above was utilized, at least partly, for the examples described below.

Example 2

As described in Example 1 but where the obtained powder was heat-treated at 70° C. for 7 days.

Figure 14:
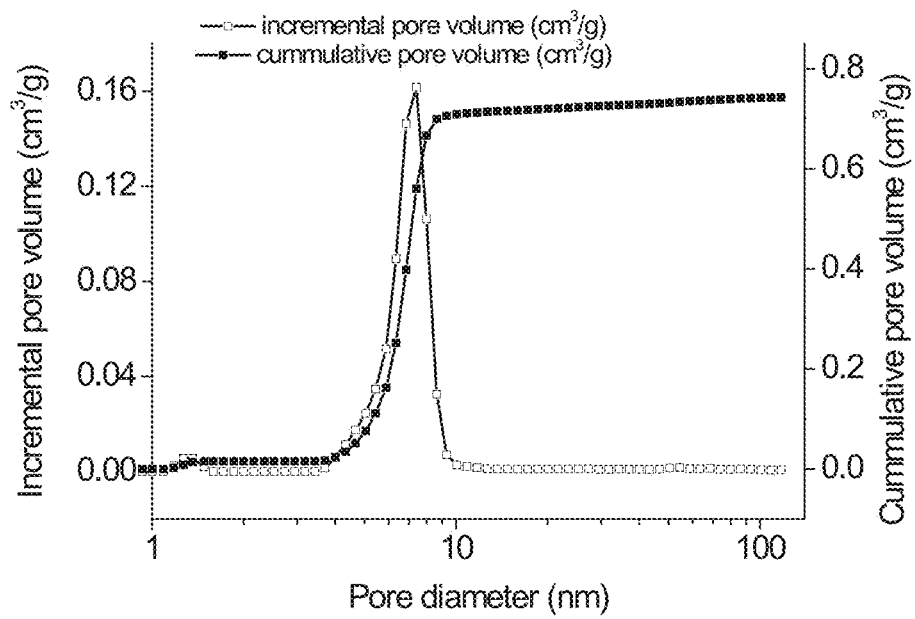
FIG. 14. is a graph illustrating the DFT-based pore size distribution for a magnesium carbonate of the present invention in which the synthesized powder was heat-treated at 70° C. for 7 days (example 2)

The particles proved to be composed of a material similar to the one in Example 1, viz. amorphous and anhydrous magnesium carbonate with traces of MgO. However, the specific surface area proved to be 454 m$^2$/g, with a distinct pore size distribution around 6 nm. As can be seen in FIG. 14 the cumulative pore volume of pores with a diameter smaller than 10 nm is above 0.7 cm$^3$/g. The nitrogen sorption isotherm and the pore size distribution obtained via DFT analysis of the nitrogen isotherm for this sample is displayed in FIGS. 13 and 14, respectively. This well-defined pore size distribution is similar to those found in ordered mesoporous silica materials and seldom found elsewhere. Also this material was associated with a H$_2$O vapor sorption isotherm similar to the one described in Example 1.

Example 3

As described in Example 1 but where the liquid was spray-dried before a gel was formed in the reaction vessel.

Figure 15:
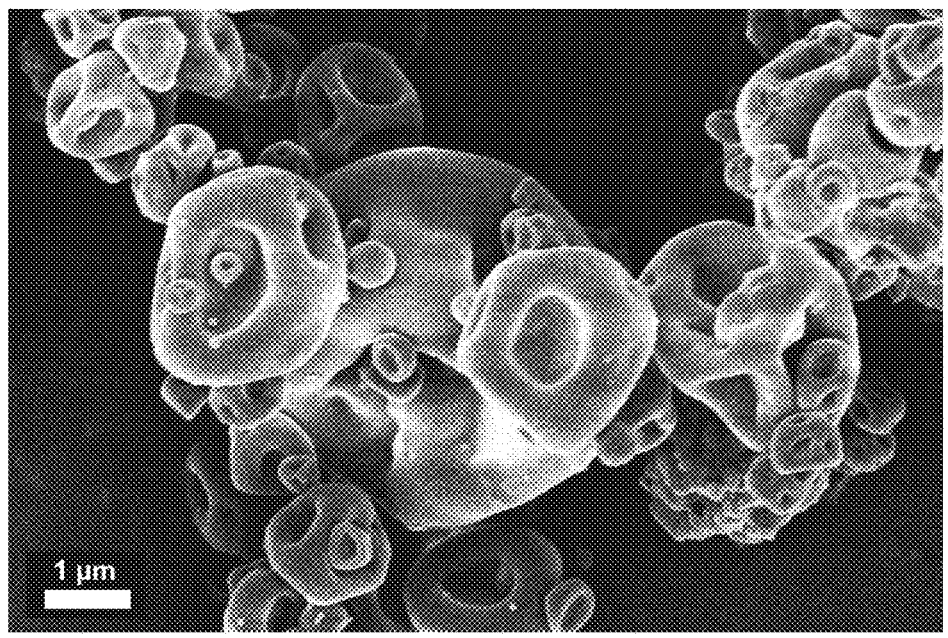
FIG. 15. Is a SEM image of a spray-dried magnesium carbonate of the present invention.
Figure 17:
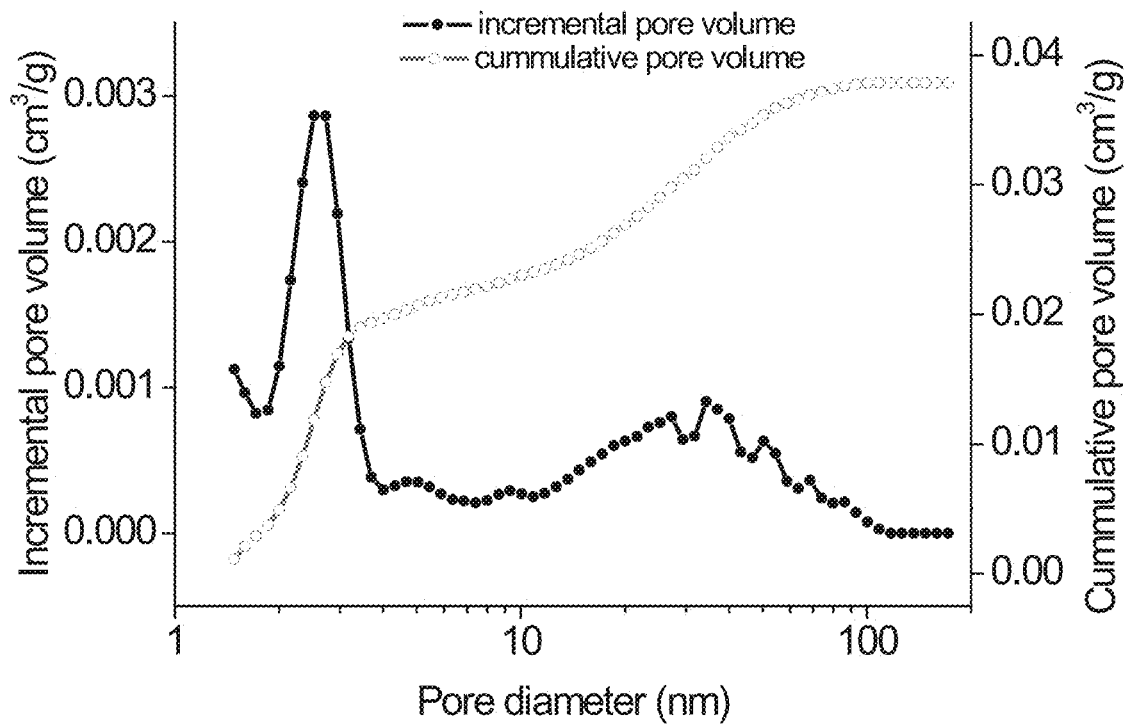
FIG. 17. is a graph illustrating the DFT-based pore size distribution of spray-dried magnesium carbonate of the present invention.
Figure 18:
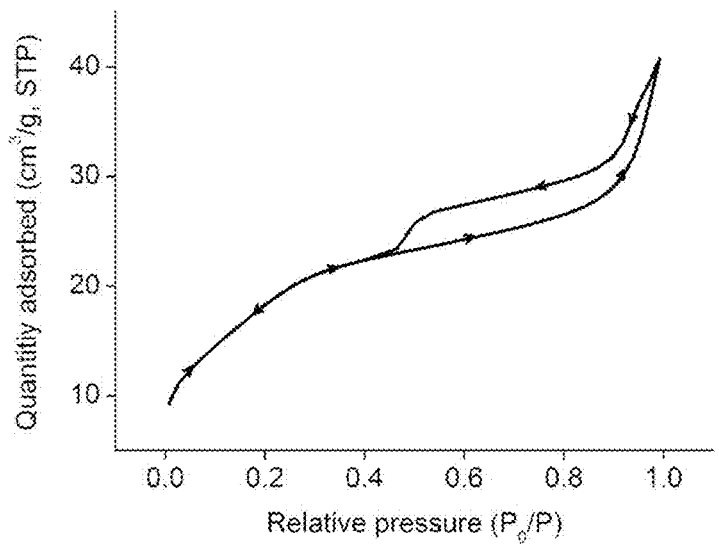
FIG. 18. is a graph illustrating the Nitrogen sorption isotherm for a spray-dried a magnesium carbonate of the present invention.
Figure 19:
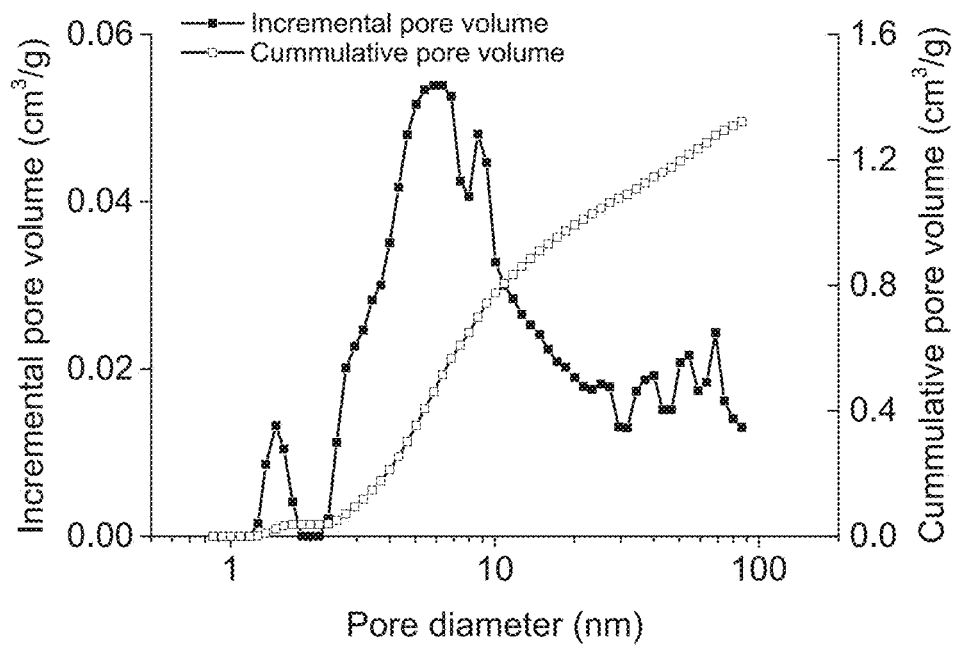
FIG. 19. is a graph illustrating the DFT-based pore size distribution for a magnesium carbonate of the present invention (example 4)

The liquid obtained after the reaction between MgO and methanol transformed into particles when spray-dried. The particles proved to be composed of a material similar to the one in Example 1, viz. amorphous magnesium carbonate with traces of MgO. The average particle size was approximately 1 m in diameter as determined by SEM analysis, SEM image in FIG. 15. The surface area of the obtained particles was 68.5 m$^2$/g as determined by BET analysis. The water vapor sorption of the spray-dried material at different RH ranging from 0-100% is displayed in FIG. 16. As can be seen in FIG. 17 the cumulative pore volume of pores with a diameter smaller than 10 nm is above 0.018 cm$^3$/g. The nitrogen sorption isotherm for the magnesium carbonate of the present invention in this example is displayed in FIG. 18.

Figure 20:
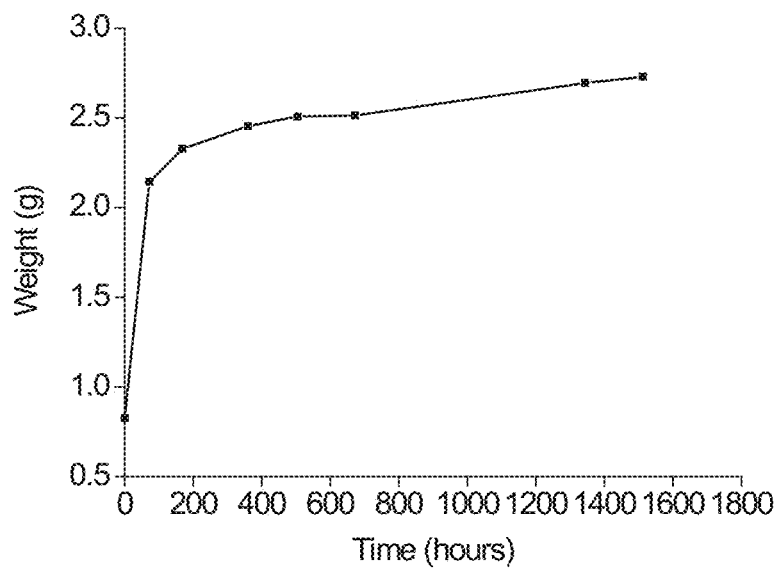
FIG. 20. is a graph illustrating the weight increase for the magnesium carbonate according to example 3 when stored in a sealed vessel saturated with water vapor at different time periods, at room temperature.
Figure 21:
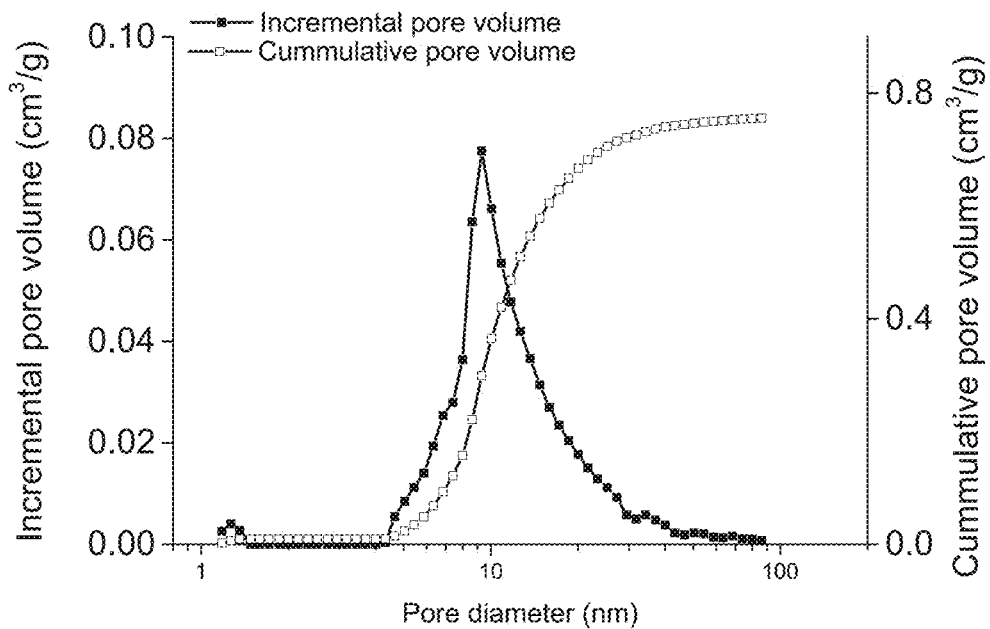
FIG. 21. is a graph illustrating the DFT-based pore size distribution for the magnesium carbonate of the present invention as prepared in example 5.
Figure 22:
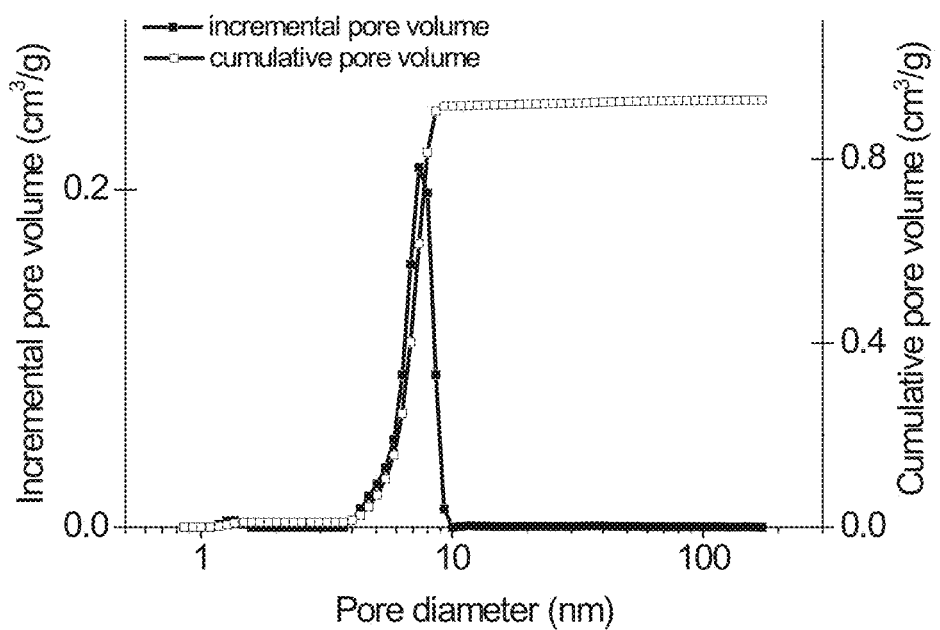
FIG. 22. is a graph illustrating the DFT-based pore size distribution for the magnesium carbonate of the present invention as prepared in example 6.
Figure 23:
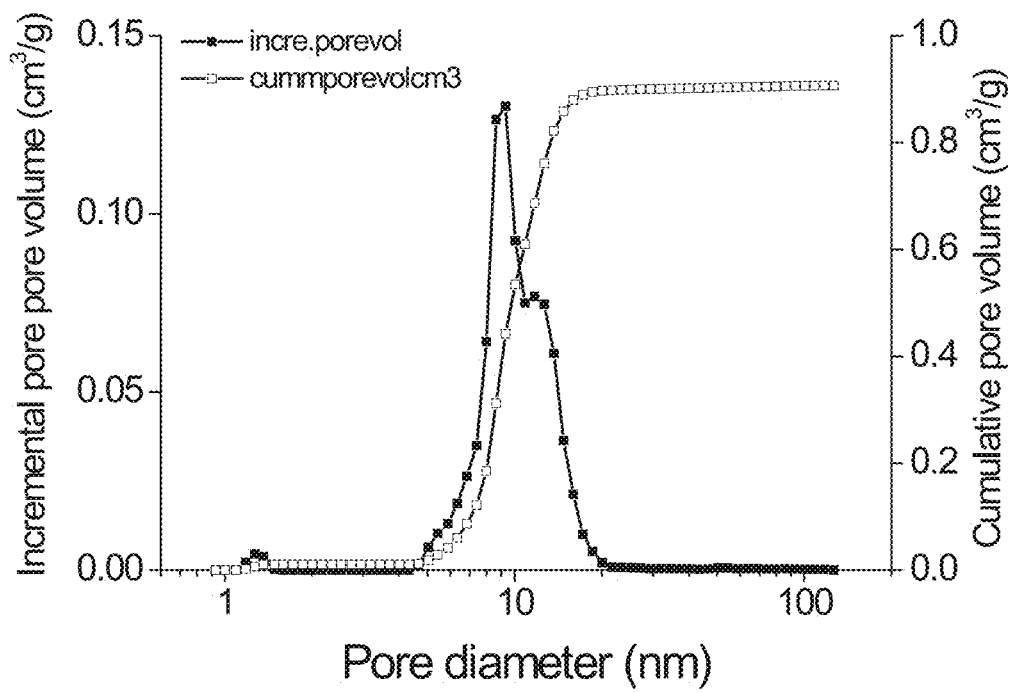
FIG. 23. is a graph illustrating the DFT-based pore size distribution for the magnesium carbonate of the present invention as prepared in example 7.
Figure 24:
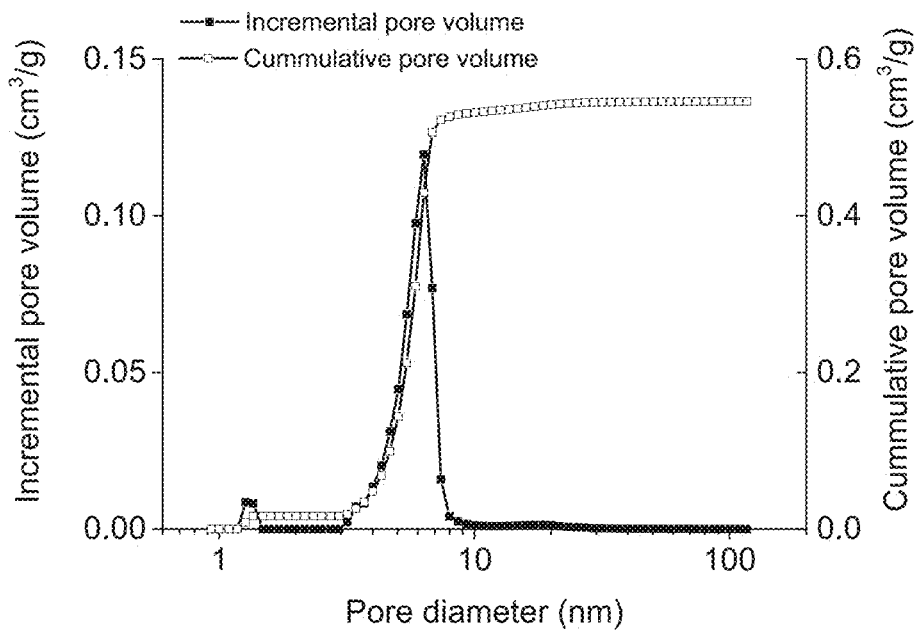
FIG. 24. is a graph illustrating the DFT-based pore size distribution for the magnesium carbonate of the present invention as prepared in example 8.
Figure 25:
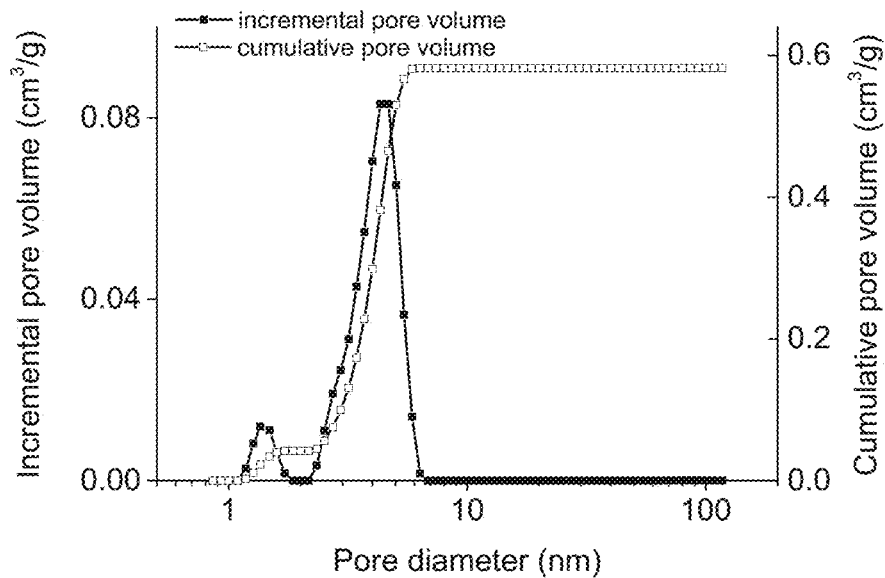
FIG. 25. is a graph illustrating the DFT-based pore size distribution for the magnesium carbonate of the present invention as prepared in example 10.

When 0.8 g dried magnesium carbonate of the present invention produced in this example was put in a sealed chamber with 100% RH at room temperature, the weight of the sample increased to 2.2 g by adsorption and uptake of water within 48 h as displayed in FIG. 20. The material continued to gain weight for several days.

Example 4

As described in Example 1 but with the material prepared with ethanol instead of methanol

| | |
|---|---|
| MgO | 8 g |
| Ethanol | 120 ml |
| CO$_2$ (gas) | 3 & 1 bar (above atmospheric pressure) |

The attempt with ethanol as solvent did not result in any visible gel formation in the reaction vessel. However, when the liquid was placed in an oven set to ≤70° C., it formed a gel that solidified and later transformed into a powder when dried. This powder contained large amounts of unreacted MgO, but it also shared some the characteristics of the previously prepared powders in Example 1. It also contained magnesium carbonate, which is suggested to be the reason for the solidification of the ethanolic liquid once placed in the oven as verified with XRD. Surprisingly, the surface area of this material was 737 m$^2$/g, which is in agreement to the magnesium carbonate produced with methanol.

After several weeks in the reaction vessel (at room temperature and atmospheric pressure) a clear gel formed at the top of the vessel. The clear gel also consisted of amorphous magnesium carbonate without traces of MgO as characterized by XRD and FT-IR. The surface area of this material is 225 m$^2$/g and a pore volume of 1.55 cm$^3$/g. The pore volume for pores less than 10 nm in width is 0.8 cm$^3$/g, see FIG. 19.

Example 5

As described in Example 1 but prepared with addition of toluene.

| | |
|---|---|
| MgO | 8 g |
| Methanol | 46 ml |
| Toluene | 74 ml |
| CO$_2$ (gas) | 3 & 1 bar (above atmospheric pressure) |

The toluene accelerated the formation of magnesium carbonate in the present example where the gelation time was reduced compared to when only methanol was used, however the surface area of the obtained material was in this case 222 m$^2$/g and the pore volume was 0.78 cm$^3$/g with a broader pore size distribution ranging from approximately 4 nm diameter to 30 nm, with a maximum at 10 nm. The volume of pores width a diameter less than 10 nm is 0.36 cm$^3$/g, see FIG. 21.

Example 6

As described in Example 1 but with a higher amount of methanol, and gel formation through increased temperature. After 4 days of reaction, the temperature in the reaction vessel was increased to 30° C. which caused the liquid to turn into a gel.

| | |
|---|---|
| MgO | 8 g |
| Methanol | 140 ml |
| CO$_2$ (gas) | 3 & 1 bar (above atmospheric pressure) |

The obtained amorphous magnesium carbonate according to the present invention proved to be composed of anhydrous and amorphous magnesium carbonate and crystalline MgO as in Example 1. The magnesium carbonate according to the present invention in this example had a surface area of 400 m$^2$/g, a pore volume of 0.97 cm$^3$/g and a narrow pore size distribution around 8 nm. The volume of pores with a pore diameter less than 10 nm is 0.91 cm$^3$/g, see FIG. 22.

Example 7

As described in Example 1 but with a higher synthesis pressure.

| | |
|---|---|
| MgO | 8 g |
| Methanol | 120 ml |
| CO$_2$ (gas) | 3 bar (above atmospheric pressure) |

In this experiment, the gas pressure was kept a 3 bar until a gel had formed in the reaction vessel. This led to a faster reaction (3 times faster) as compared to Example 1. The obtained material proved once more to consist of amorphous and anhydrous magnesium carbonate with traces of MgO as described in Example 1. The surface area measured via gas adsorption for the material obtained in this experiment was 309 m$^2$/g with a pore volume of 0.575 cm$^3$/g. The DFT-based pore size distribution showed pore diameters between 4-8 nm, with a maximum around 6 nm. The volume of pores with diameter less than 10 nm is 0.53 cm$^3$/g, see FIG. 23.

Example 8

As described in Example 1 but with a lower amount of MgO, and gel formation through increased temperature. After 4 days of reaction, the temperature in the reaction vessel was increased to 40° C. which caused the liquid to turn into a gel.

| | |
|---|---|
| MgO | 6 g |
| Methanol | 120 ml |
| CO$_2$ (gas) | 1 bar & 3 bar (above atmospheric pressure) |

The obtained magnesium carbonate according to the present invention proved to be composed of anhydrous and amorphous magnesium carbonate and crystalline MgO as in Example 1. The surface area of the obtained material was 284 m$^2$/g with a total pore volume of 0.93 cm$^3$/g and a narrow pore size distribution around 8.5 nm. The volume of pores with diameter less than 10 nm is 0.54 cm$^3$/g, see FIG. 24.

Example 9

As described in Example 1 but with a lower synthesis temperature.

| | |
|---|---|
| MgO | 8 g |
| Methanol | 120 ml |
| CO$_2$ (gas) | 3 & 1 bar (above atmospheric pressure) |

In this experiment, the reaction temperature was kept at room temperature until a gel had formed in the reaction vessel. This led to a significantly slower reaction as compared to Example 1. The obtained material proved once more to consist of amorphous and anhydrous magnesium carbonate with traces of MgO as described in Example 1 with similar characteristics.

Example 10

As described in Example 1 but with addition of various amounts of CaO.

| | |
|---|---|
| MgO/Ca(OH)$_2$ ratio | 1:1-1:0 (8 g) |
| Methanol | 120 ml |
| CO$_2$ (gas) | 3 & 1 bar (above atmospheric pressure) |

Increasing amounts of Ca(OH)$_2$ in the powder phase prior to the reaction led to increasing amounts of amorphous CaCO$_3$ in the resultant material. Storing the materials at high relative humidities for an extended time crystallized the amorphous CaCO$_3$ content in the amorphous magnesium carbonate according to the present inventions. Amorphous and anhydrous magnesium carbonate was still obtained throughout the experiments.

When prepared with 5 wt % Ca(OH)$_2$ in the powder phase, the surface area of the material of the present invention was 570 m$^2$/g, with a total pore volume 0.63 cm$^3$/g and a narrow pore size distribution around 4.5 nm. The volume of pores with diameter less than 10 nm is 0.58 cm$^3$/g, see FIG. 25.

Example 11

As described in Example 1 but with addition of various amounts of SrO.

| | |
|---|---|
| MgO/SrO ratio | 1:1-1:0 (8 g) |
| Methanol | 120 ml |
| CO$_2$ (gas) | 3 & 1 bar (above atmospheric pressure) |

Increasing amounts of SrO in the powder phase prior to the reaction led to increasing amounts of crystalline SrCO$_3$ in the resultant material. Amorphous and anhydrous magnesium carbonate was still obtained throughout the experiments.

Example 12

As described in Example 1 but with addition of various amounts of BaO.

| | |
|---|---|
| MgO/BaO ratio | 1:1-1:0 (8 g) |
| Methanol | 120 ml |
| $CO_2$ (gas) | 3 & 1 bar (above atmospheric pressure) |

Increasing amounts of BaO in the powder phase prior to the reaction led to increasing amounts of crystalline $BaCO_3$ in the resultant material. Amorphous and anhydrous magnesium carbonate was still obtained throughout the experiments.

Example 13

As in example 3 but spin coated instead of spray dried.
The liquid was spin coated onto a silicon wafer and dried at 70° C., which resulted in a coating of amorphous magnesium carbonate according to the present invention on the silicon wafer.

Example 14

As in Example 3 but where the liquid was filtered through a filter membrane having a pore size cut-off of at about 200 nm to obtain a clear, transparent liquid. The liquid was then stored at 1 bar (above atmospheric pressure) with $CO_2$ gas until a gel was formed. The gel was then transferred onto a tray and placed in an oven at 70° C. to solidify and dry. The obtained product consisted of high purity anhydrous and amorphous magnesium carbonate of the present invention.

Example 15

As described in Example 1 but where reaction vessel was depressurized before a gel had formed (after 3 days of reaction) and where the liquid was left in the vessel at room temperature and ambient conditions for 2 weeks before placed in an oven at 70° C.

| | |
|---|---|
| MgO | 8 g |
| Methanol | 120 ml |
| $CO_2$ (gas) | 3 & 1 bar (above atmospheric pressure) |

Figure 26:
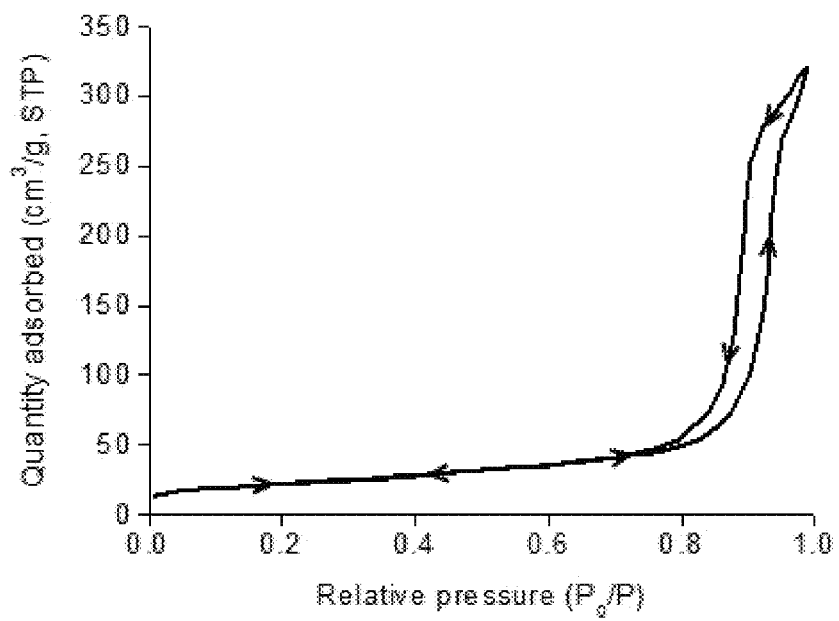
FIG. 26. is a graph illustrating the nitrogen sorption of the magnesium carbonate material as prepared in example 15.
Figure 27:
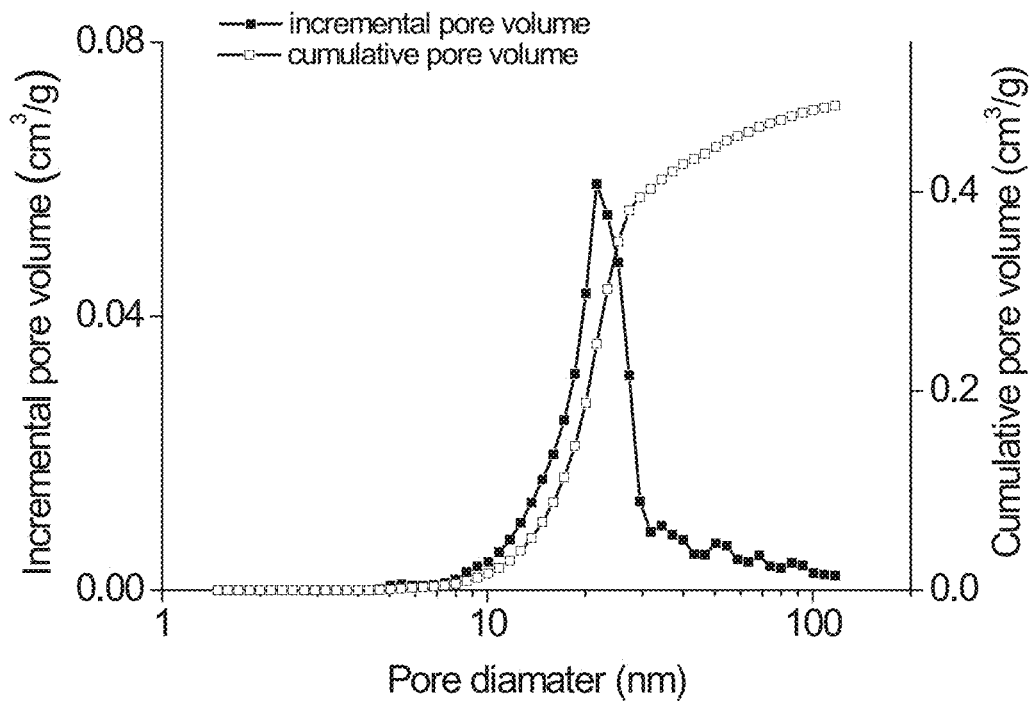
FIG. 27. is a graph illustrating the DFT-based pore size distribution for the magnesium carbonate material as prepared in example 15.

The liquid formed in the reaction vessel transformed into a gel when it was left standing for 24 at ambient conditions. When the gel was placed in the oven after 2 weeks it solidified and the material was dried out. This produced a solid material with the same composition as described in Example 1, i.e. amorphous and anhydrous magnesium carbonate with traces of MgO. However, the SSA of the final material in this example was substantially lower (77 m2/g) as compared to the material in Example 1 and had a total pore volume of 0.47 cm$^3$/g with a distinct pore size distribution around 20 nm, see FIGS. 26 and 27. The pore volume corresponding to pores smaller than 10 nm in diameter was only 0.0043 cm$^3$/g in this example, as illustrated in FIG. 27, which essentially corresponds to an absence of micro pores according to the definition used herein. The absence of micro pores and the low pore volume in the final material produced in this example caused a drastic decrease in water vapor sorption capacity as compared with the materials in Examples 1 and 2. The water sorption characteristics of the material in this example is displayed in FIG. 28.

Example 16

As described in Example 1 but with various temperatures and pressures during the initial stage of the synthesis reaction. The initial stage of the reaction is the time it takes for the slightly yellow liquid to form (approx. 3 hours in Example 1).

| | |
|---|---|
| MgO | 8 g |
| Methanol | 120 ml |
| Initial reaction $CO_2$ pressure | 0.001 bar to 79 bar (above atmospheric pressure) |
| Initial reaction temperature | From 0° C. to just below boiling temperature (max 100° C.) |
| Later reaction $CO_2$ pressure | 1 bar (above atmospheric pressure) |
| Later reaction temperature | 25° C. |

The boiling temperature of methanol varies with pressure and hence the synthesis temperature in this example was adjusted so that the methanol never did boil at the current pressure. Increasing temperatures and pressures in the initial reaction stage resulted in faster formation of the slightly yellow liquid in the reaction vessel. At the lower temperatures and pressures, a change in color was not observed visually and the initial stage of the reaction was terminated after 6 hours. A lower yield of magnesium carbonate was obtained in the final materials for the synthesis performed at low initial temperature and pressure.

Example 17

As described in Example 1 but with various temperatures and pressures during the later stage of the synthesis reaction. The later reaction stage is the phase of the reaction that follows when preferably the slightly yellow liquid has formed.

| | |
|---|---|
| MgO | 8 g |
| Methanol | 120 ml |
| Initial reaction $CO_2$ pressure | 3 bar (above atmospheric pressure) |
| Initial reaction temperature | 50° C. |
| Later reaction $CO_2$ pressure | 0.001 bar to 79 bar (above atmospheric pressure) |
| Later reaction temperature | From 0° C. to below boiling (max 100° C.) |

The boiling temperature of methanol varies with pressure and hence the synthesis temperature in this example was adjusted so that the methanol never did boil at the pressure used. The highest yield of magnesium carbonate in the final materials was obtained at pressures around 1 bar (above atmospheric pressure) and temperatures below 50° C. However, various amounts of magnesium carbonate were obtained throughout the experiments.

Example 18

As described in Example 1 but with higher temperatures during the solidification step.

| | |
|---|---|
| Methanol | 120 ml |
| $CO_2$ (gas) | 3 & 1 bar (above atmospheric pressure) |
| Solidification temperature | 75° C. to 300° C. |

This produced magnesium carbonate materials with similar characteristics as in Example 1.

Example 19

As described in Example 1 but with lower temperatures during the solidification step.

| | |
|---|---|
| Methanol | 120 ml |
| $CO_2$ (gas) | 3 & 1 bar (above atmospheric pressure) |
| Solidification temperature | 25° C. and below |

This produced amorphous and low surface area materials.

Example 20

As described in Example 1 but below freezing temperature of methanol.

| | |
|---|---|
| MgO | 8 g |
| Methanol | 120 ml |
| $CO_2$ (gas) | 3 & 1 bar (above atmospheric pressure) |

In this case no reaction occurred.

Example 21

As in Example 1 but prepared with pentane instead of methanol

| | |
|---|---|
| MgO | 8 g |
| Pentane | 120 ml |
| $CO_2$ (gas) | 3 & 1 bar (above atmospheric pressure) |

In this case no reaction occurred.

Example 22

As described in Example 1 but with addition of various amounts of water

| | |
|---|---|
| MgO | 8 g |
| Methanol | 120 ml |
| $H_2O$ | 5-100 ml |
| $CO_2$ (gas) | 3 & 1 bar (above atmospheric pressure) |

In this case, crystalline phases of magnesium carbonates were formed. At higher water concentrations the resultant materials were hydrated while the materials formed at lower water concentrations were of more anhydrous nature.

Example 23

As described in Example 1 but where the $CO_2$ was bubbled through the methanolic suspension of MgO.

| | |
|---|---|
| MgO | 8 g |
| Methanol | 120 ml |

In this case no reaction occurred.

Example 24

As described in Example 1 but with 50 volumetric percent of water.

| | |
|---|---|
| MgO | 8 g |
| Methanol | 60 ml |
| $H_2O$ | 60 ml |
| $CO_2$ (gas) | 3 & 1 bar (above atmospheric pressure) |

Figure 29:
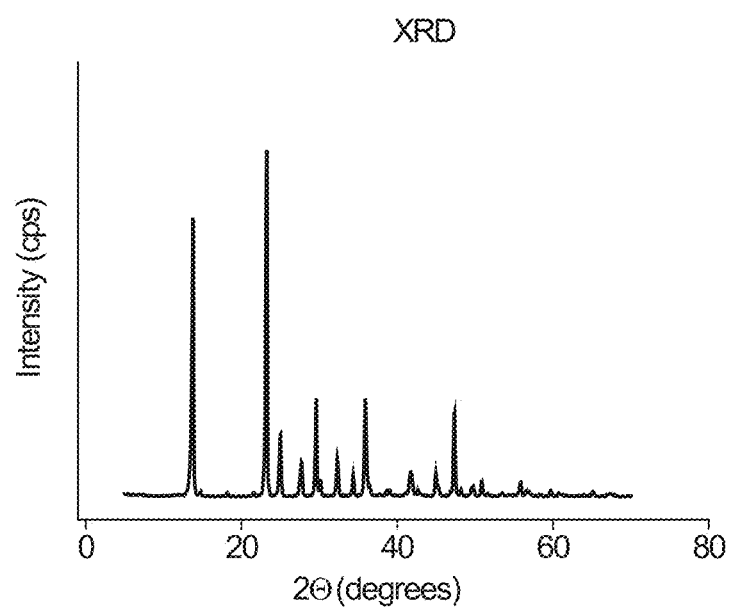
FIG. 29. Illustrates the X-ray diffraction pattern for the material as prepared in example 24, wherein the peaks correspond to crystalline nesquehonite.

In this case, crystalline nesquehonite was formed, see FIG. 29. The material had a low surface area and was non-porous and hence the presence of 60 ml water in 60 ml methanol does not lead to the desired result.

Example 25

As described in Example 1 but with $Mg(OH)_2$ instead of MgO as the starting material.

| | |
|---|---|
| $Mg(OH)_2$ | 8 g |
| Methanol | 120 ml |
| $CO_2$ (gas) | 1 & 3 bar (above atmospheric pressure) |

In this case no reaction occurred, hence the use of $Mg(OH)_2$ as a starting material when using the same reaction conditions as in example 1 does not lead to the desired result.

Example 26

As described in Example 1 but with $Mg(OCH)_3$ instead of MgO as the starting material.

| | |
|---|---|
| $Mg(OCH)_3$ | 50 ml (10 wt % $Mg(OCH_3)_2$ in methanol) |
| $CO_2$ (gas) | 1 & 3 bar (above atmospheric pressure) |
| Water | 0.87 ml |

Figure 32:
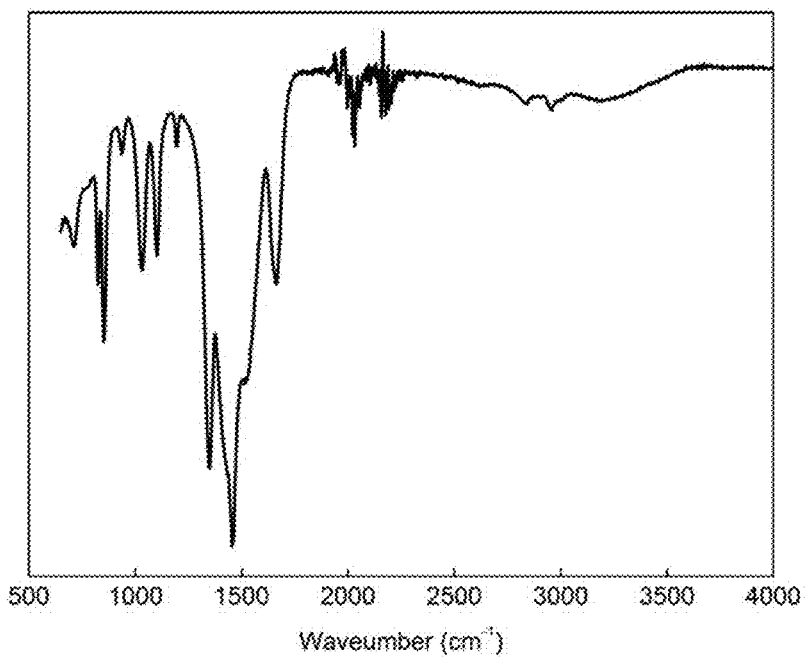
FIG. 32. is a graph illustrating the IR spectrum for the material as prepared in example 26.

In this example the magnesium methoxide and water were placed in a reaction vessel under carbon dioxide pressure, the carbon dioxide pressure was set to 3 bar above atmospheric pressure for the first 3 hours and then lowered to 1 bar above atmospheric pressure for the remaining reaction time. The temperature was set to 50° C. for the first 3 hours and then room temperature for the remaining reaction time. The solution in the reaction vessel turned yellow within 1 hour and after 12 hours a powder had formed in the reaction vessel, this powder was characterized as magnesium methyl carbonate based on the IR spectra in FIG. 32. Hence in this example no magnesium carbonate was formed and therefore using these conditions $Mg(OCH_3)_2$ is not a preferred starting material.

Example 27

Figure 33:
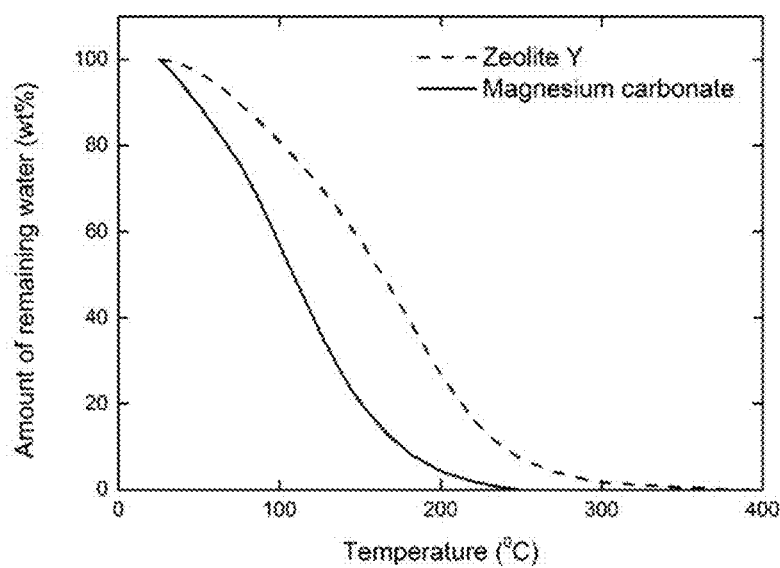
FIG. 33. is a graph illustrating the regeneration temperature needed to remove adsorbed water from the magnesium carbonate as prepared in example 27 as compared to Zeolite.

The magnesium carbonate material was prepared as in the specific example using a drying/calcination temperature of 250° C. In this example the magnesium carbonate material and the zeolite Y material were dried at 250° C. over night, after this both the samples were placed in a desiccator saturated with water vapor, i.e. 100% relative humidity, at room temperature for 18 hours. After this the regeneration energy were compared between the two samples using a TGA instrument, more precisely a Thermogravimetric analyzer from Mettler Toledo, model TGA/SDTA851e instrument with a 3° C./min ramping temperature was used. The measurements were performed under a flow of air. The result is shown in FIG. 33, as can be seen in the figure at 150° C. the magnesium carbonate material according to the present invention has lost 40 wt % more water than the Zeolite Y and approximately 65° C. higher temperature is needed for a complete removal of water in the zeolite Y material as compared to the magnesium carbonate material.

Example 28

In this example the magnesium carbonate according to the current invention is used as a pharmaceutical excipient. As an illustrative example amorphous Ibuprofen was formulated using the magnesium carbonate according to the present invention.

Introduction to Example 28 During the last decades, poor aqueous solubility of active pharmaceutical ingredients (APIs) has been one of the most challenging issues for the pharmaceutical industry. About 40% of newly marketed drugs have low solubility and 80-90% of drug candidates in the R&D pipeline fail due to solubility problems. Due to the poor aqueous solubility these drugs have low bioavailability and/or a slow onset of action, and this may lead to a limited and insufficient therapeutic effect. Therefore, much effort has been put into solving this issue using different types of strategies including salt formulations, API particle size reduction, use of solubilizers, solid dispersions, co-ground mixtures and pro-drugs. However, there are still practical limitations of these techniques. For example, the salt formation is available for acid and basic drugs, however it is not feasible for neutral compounds and it may be difficult to form salts of very weak bases and acids. Even if a stable salt can be formed, conversion from a salt to a poorly soluble free acid or base can occur both in vitro and in vivo; as to the particle size reduction, this method may lead to build-up of static charges and lead to handling difficulties In this respect, preparation and stabilization of the API in its amorphous state have been suggested. Typically, organic polymers like polyethylene glycol (PEG) and polyvinyl pyrroline (PVP) are used in solid dispersions for this purpose. However, this approach suffers from the problems with chemical stability of products and difficulties in the industrial manufacturing processes. Recent developments in nanotechnology science have provided new inorganic materials that can be used to stabilize amorphous APIs. It has been found that mesoporous structures (pores with a diameter between 2 and 50 nm) in materials have the ability to effectively supress crystallisation of amorphous substances.

Materials Synthesis for Example 28

Magnesium Oxide (MgO) and ibuprofen were obtained from Sigma-Aldrich, Sweden. Methanol and ethanol were purchased from VWR International, Sweden. $CO_2$ was obtained from Air Liquide, Sweden. All chemicals were used as received.

The magnesium carbonate was synthesised as follows: 170 g of MgO and 2.5 L $CH_3OH$ was mixed at 500 rpm in a 5 L Ecoclave pressure reactor from Büchi. The reactor was pressurised with 3 bar $CO_2$ and the reaction was carried out at 55° C. After 4 days the temperature was lowered to room temperature and the reactor depressurised. The product was dried at 75° C. in a vacuum oven for 3 days and then calcined at 250° C. for 6 hours. Calcination was performed in order to assure decomposition of the organic intermediates formed in the reaction carried out in the pressure reactor. Upon this decomposition, magnesium carbonate is formed.

Drug Loading Procedure for Example 28

Ibuprofen was incorporated into the magnesium carbonate via a soaking method; 203.2 mg ibuprofen was dissolved in 50 ml ethanol and then 642.7 mg of the magnesium carbonate was added to the solution. The mixture was placed on an orbital shaker at 100 rpm at room temperature for 24 h to allow for diffusion of ibuprofen into the magnesium carbonate. Subsequently the suspension was dried in an oven at 70° C. to evaporate the solvent leaving a dry product containing 24 wt % of Ibuprofen.

Characterization for Example 28

X-ray powder diffraction (XRD) analysis was performed with a D5000 diffractometer (40 kV, 40 mA, Siemens/Bruker) using Cu-$K_\alpha$ radiation ($\lambda$=0.154 nm). Samples were ground in a mortar and put on silicon sample holders with zero background prior to analysis.

Fourier transform infrared spectroscopy (FTIR) studies were performed, using a Bruker FTS 66v/s spectrometer with an Attenuated Total Reflectance (ATR) sample holder. All FTIR spectra were collected at a spectrum resolution of 4 $cm^{-1}$, with 50 scans over the range from 4,000 to 500 $cm^{-1}$. A background scan was acquired before scanning the samples.

$N_2$ sorption analysis. Gas sorption isotherms were obtained using an ASAP 2020 from Micromeritics, operated at 77 K. Prior to analysis the samples were degassed under vacuum at 338 K for 12 h prior to measurement. The specific surface area (SSA) was calculated using the multipoint Brunauer-Emmett-Teller (BET) method while the pore size distribution was calculated based on density functional theory (DFT) method using the model for $N_2$ at 77 K. These calculations were all performed using the ASAP 2020 (Micromeritics) software.

Thermal gravimetric analysis (TGA) was carried out on a Mettler Toledo, model TGA/SDTA851e, under an air flow in an inert alumina cup. The samples were heated from room temperature to 600° C. with a heating rate of 3 K $min^{-1}$.

Differential scanning calorimetry (DSC) was performed on a DSC Q2000 instrument from TA instruments using Exstar software. Samples of 3.5-5.5 mg were weighted into 5 mm Al pans and sealed. Samples were first cooled down to ~35° C. and then heated to 150° C. at a heating rate of 3K $min^{-1}$. The instrument was calibrated for melting point and hear of fusion ($Tm[° C.]$ and $\Delta Hm[mJ\ mg^{-1}]$) of Indium (156.6° C., 28.4 mJ $mg^{-1}$).

Drug Release Measurement: The release of ibuprofen was carried out in a USP-2 dissolution bath (Sotax AT7 Smart, Sotax AG, Switzerland) equipped with 1000 mL vessels (37°

C., 50 rpm). Samples with a total drug content of 17.5 mg ibuprofen were placed in vessels containing 500 mL phosphate buffer (pH=6.8). Measurements were made in triplicates on pure ibuprofen (IBU) crystals and ibuprofen loaded magnesium carbonate (MGCO3-IBU). Aliquots of 3 mL were withdrawn from each vessel at regular intervals for 125 min and the drug concentration in the liquid samples was analysed using UV/vis absorbance spectroscopy (1650PC, Shimadzu Corporation, Kyoto, Japan).

Long-term Stability Test: An MGCO3-IBU sample was stored in a desiccator at room temperature and 75% RH (obtained with a saturated aqueous mixture of water and NaCl) for 3 months. The sample was then analysed with XRD and DSC in order to investigate if a humid atmosphere induces crystallisation of the incorporated ibuprofen. Magnesium carbonate without ibuprofen was also stored under the same conditions to examine if the humidity affects the carrier material.

Results for Example 28 After calcination, the Magnesium carbonate was in the form of white millimetre-sized particles.

The peaks in the obtained XRD pattern correspond to unreacted MgO in the product while the lack of other peaks revealed that the magnesium carbonate component in the material is amorphous. The magnesium carbonate component of the material was evident from the FTIR spectra of the material, where absorption bands at ~850 $cm^{-1}$, ~1100 $cm^{-1}$ and ~1400 $cm^{-1}$ stem from the carbonate group. The pore volume and mean pore size of the magnesium carbonate, as obtained from analysis of nitrogen sorption isotherms, are given in table 3 below.

TABLE 3

Results of material characterizations before and after ibuprofen loading as obtained from $N_2$ sorption experiments. The BET surface area was obtained as in above examples.

| Sample | $S_{BET}$ ($m^2/g$) | $V_{pore}$ ($cm^3/g$) | $D_{BJH}$ (nm) |
|---|---|---|---|
| Magnesium carbonate | 349 | 0.833 | 6.9 |
| MGCO3-IBU | 245 | 0.394 | 4.9 |

Figure 34:
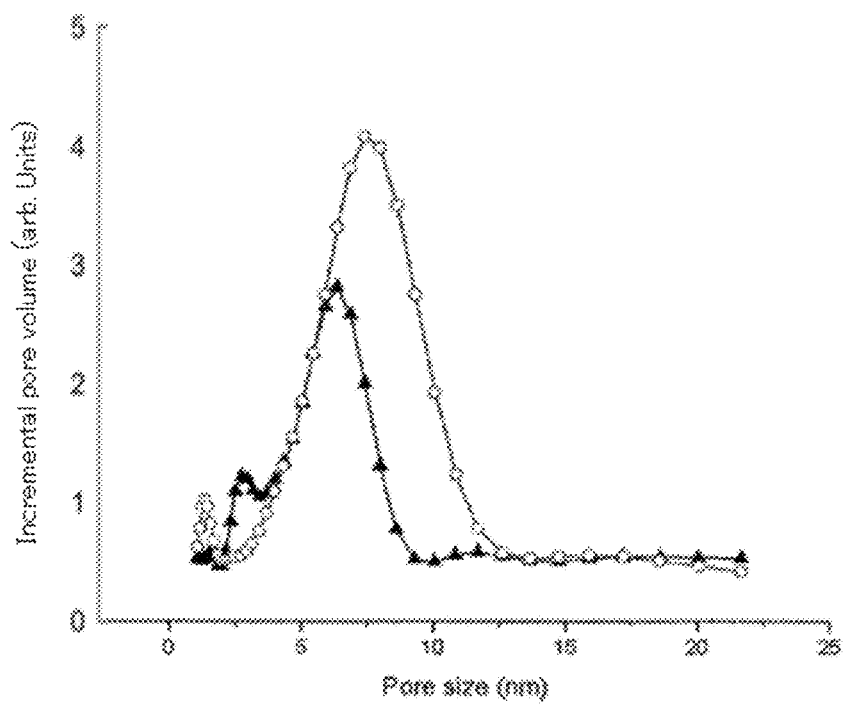
FIG. 34. is a graph illustrating the pore size distribution (incremental pore volume in a.u.) obtained from the $N_2$ sorption analysis of isotherms recorded on the calcined magnesium carbonate material as prepared in example 28 (curve with open circles) as well as on the ibuprofen loaded MGCO3-IBU sample (curve with solid triangles) of the same example.

The pore size distribution obtained from the $N_2$ sorption analysis is given in FIG. 34 After loading the magnesium carbonate with ibuprofen, TGA was carried out to investigate the drug loading degree in the carrier. From these it was evident that the free ibuprofen decomposed at about 200° C. while the magnesium carbonate in the calcined material before drug loading decomposed into MgO and $CO_2$ at about 370° C. For the MGCO3-IBU sample two distinct weight loss regions were observed, the first related to the decomposition of ibuprofen and the other related to the decomposition of the magnesium carbonate. The decomposition temperature of the incorporated ibuprofen was shifted 140° C. to about 340° C. compared to the free substance. The onset of decomposition for the magnesium carbonate was also shifted towards higher temperatures in the MGCO3-IBU sample, from about 320° C. to 350° C. compared to the calcined and unloaded material. From the TGA data it can be calculated that the drug loading degree of ibuprofen in MGCO3-IBU is 24 wt % which corresponds to the magnesium carbonate/ibuprofen weight ratio in the preparation of the sample.

FTIR for MGCO3-IBU further confirmed successful incorporation of ibuprofen in the magnesium carbonate. In the absorbance spectra for the MGCO3-IBU, no new absorbance bands compared to the free ibuprofen and the empty magnesium carbonate could be observed. This indicated that the adsorption of the ibuprofen in the pores of the magnesium carbonate was of physical character.

From the $N_2$ sorption data it can be seen that the mean pore diameter in the MGCO3-IBU sample is reduced with 2 nm compared to the empty magnesium carbonate and that the pore volume is reduced by about 50%. The shift toward smaller pores related to narrowing of the pores in the empty magnesium carbonate when the material is filled with ibuprofen is also seen in the pore size distribution in FIG. 34.

The XRD pattern for MGCO3-IBU lacks peaks corresponding to crystalline ibuprofen indicating a lack of crystallinity of the incorporated drug. The only peaks visible in the MGCO3-IBU XRD pattern stem from the MgO in the material. The lack of crystallinity of the ibuprofen in the MGCO3-IBU sample was further evident from the DSC curves. The endothermic event observed in these curves at 78° C. for the free, crystalline ibuprofen corresponds to melting of the crystalline structure. The complete lack of an endothermic event at the same temperature for the MGCO3-IBU sample confirmed that the incorporated ibuprofen was not present in a crystalline state inside the pores. No peaks corresponding to any endo- or exothermic events could be detected in the DSC scan between ~35° C. to 150° C. for the MGCO3-IBU sample. The XRD and DSC data shows that the the magnesium carbonate according to the invention supresses crystallisation of the incorporated ibuprofen.

Figure 35:
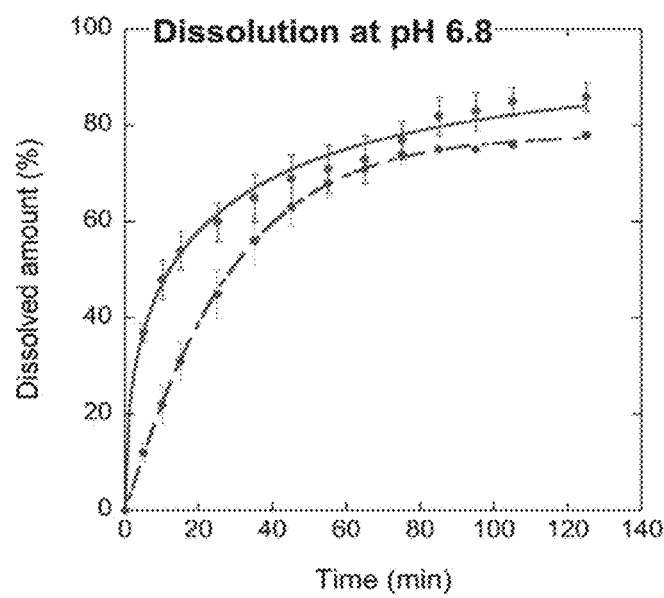
FIG. 35. is a graph illustrating the dissolution profile of free ibuprofen (dashed lower curve) and ibuprofen incorporated in the magnesium carbonate as prepared in example 28 (solid upper curve) recorded at pH 6.8.

The dissolution profile of free ibuprofen and ibuprofen formulated with the magnesium carbonate can be seen in FIG. 35. The dissolution rate of the amorphous ibuprofen formulated with the magnesium carbonate according to the present invention is more rapid compared to the free substance. The dissolution rate for the amorphous ibuprofen is about three times faster during the first 5 minutes compared to the free substance and about 50% of the ibuprofen is dissolved and released from the carrier within 12 minutes while it takes about 30 minutes for the free substance to dissolve to the same level. The apparent solubility of the amorphous ibuprofen formulated with the magnesium carbonate according to the present invention is higher compared to the free substance.

In the stability test, no signs of crystallisation of the ibuprofen formulated with the magnesium carbonate could be detected with XRD and DSC after that the sample had been stored at 75% RH for three months at room temperature. Neither could any signs of crystallisation of the amorphous magnesium carbonate component in the formulation be detected when exposed to the humid atmosphere.

As appreciated by the skilled person the drug Ibuprofene should be considered as a non-limiting example of the use of the magnesium carbonate according to the present invention as a pharmaceutical or cosmetical excipient in combination with an active substance. In the case that the active substance is amorphous, crystallisation of the substance may be completely or partly suppressed by the magnesium carbonate leading to faster dissolution rate and/or increased solubility of the substance. The magnesium carbonate of the present invention is not only expected to act as a solubility enhancer when used as an excipient but also as, e.g., a pH modifier, tablet and capsule diluent, adsorbent, anti-caking agent and free-flowing agent.

Example 29

Figure 36:
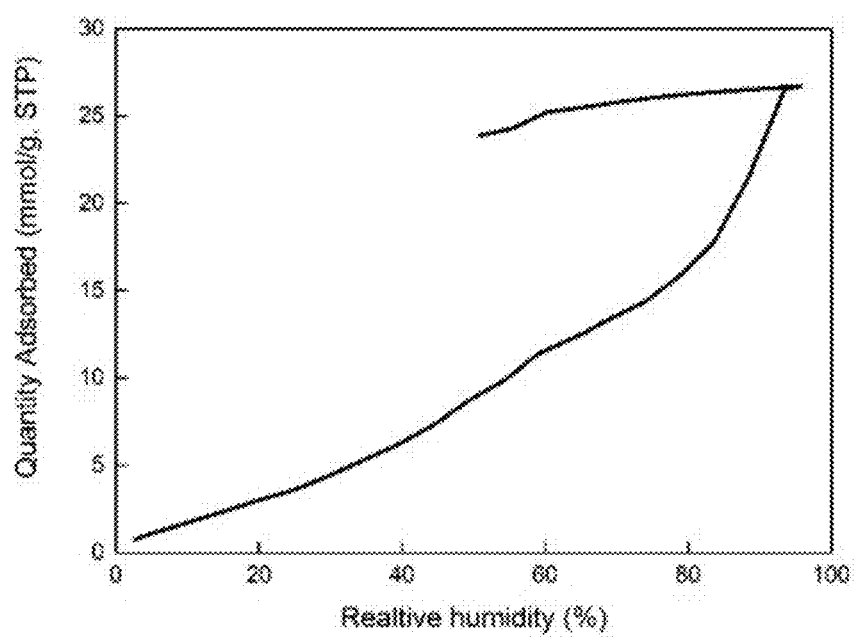
FIG. 36. is a graph illustrating the water sorption isotherms at room temperature for a calcined magnesium carbonate of the present invention as prepared in example 29.

The magnesium carbonate material was prepared as in as in the specific example described above with the alteration that the first drying time was reduced from 3 to 2 days. After 3 months of storage at 70 C the material was dried/calcined using a temperature of 300° C. The water sorption capacity of the calcined amorphous magnesium carbonate according to the invention was determined in the same way as described in example 1 with references to FIG. 5. The result for the calcined material is illustrated in FIG. 36. The measurements shows that the amorphous magnesium carbonate according to the present invention after calcination adsorbs more than 0.6 mmol water/g material and even more than 0.7 mmol water/g material at an RH of 3% at room temperature. At an RH of 10% at room temperature the calcined amorphous magnesium carbonate adsorbs more than 1.5 mmol water/g material and even more than 1.7 mmol water/g material. At an RH of 90% at room temperature the calcined amorphous magnesium carbonate adsorbs more than 15 mmol water/g material and even more than 20 mmol water/g material.

Although the present invention has been described in connection with preferred embodiments thereof, it will be appreciated by those skilled in the art that additions, deletions, modifications, and substitutions not specifically described may be made without department from the spirit and scope of the invention as defined in the appended claims.

What is claimed is:

1. A mesoporous composite carbonate material comprising:
    X-ray amorphous and anhydrous magnesium carbonate; and
    a second component,
    wherein the second component is calcium carbonate,
    wherein a maximum value in an incremental pore volume distribution in $cm^3/g$ of the mesoporous composite material occurs for pores with a diameter of 10 nm or less,
    wherein the incremental pore volume distribution is measured by nitrogen sorption,
    wherein the mesoporous composite carbon material with pores with a diameter of 10 nm or less has a cumulative pore volume distribution of at least 0.2 $cm^3/g$, and
    wherein the cumulative pore volume distribution is measured by nitrogen sorption.

2. The mesoporous composite carbonate material according to claim 1, wherein the mesoporous composite carbonate material is characterized by a BET specific surface area obtained from $N_2$ sorption isotherms of between 60 $m^2/g$ and 1500 $m^2/g$.

3. The mesoporous composite carbonate material according to claim 2, wherein the BET specific surface area is between 100 $m^2/g$ and 1500 $m^2/g$.

4. The mesoporous composite carbonate material according to claim 3, wherein the BET specific surface area is between 240 $m^2/g$ and 1500 $m^2/g$.

5. The mesoporous composite carbonate material according to claim 4, wherein the BET specific surface area is between 500 $m^2/g$ and 1500 $m^2/g$.

6. The mesoporous composite carbonate material according to claim 1, wherein the maximum value in the incremental pore volume distribution in $cm^3/g$ of the mesoporous composite material occurring for pores with a diameter of 10 nm or less is 0.2 $cm^3/g$.

7. The mesoporous composite carbonate material according to claim 1, wherein the maximum value in the incremental pore volume distribution in $cm^3/g$ of the mesoporous composite material occurring for pores with a diameter of 10 nm or less is from 0.04 to 0.16 $cm^3/g$.

8. The mesoporous composite carbonate material according to claim 1, wherein the cumulative pore volume distribution is at least 0.5 $cm^3/g$.

9. The mesoporous composite carbonate material according to claim 1, including up to 50 wt % calcium carbonate.

10. A desiccant comprising the mesoporous composite carbonate material according to claim 1.

11. A pellet or a film comprising the mesoporous composite carbonate material according to claim 1.

12. An additive to a food, a chemical, a cosmetic or a pharmaceutical comprising the mesoporous composite carbonate material according to claim 1.

13. An excipient in a cosmetic or a pharmaceutical comprising the mesoporous composite carbonate material according to claim 1.

14. A mesoporous composite carbonate material comprising:
    calcium carbonate; and
    X-ray amorphous and anhydrous magnesium carbonate,
    wherein a maximum value in an incremental pore volume distribution in $cm^3/g$ of the mesoporous composite material occurs for pores with a diameter between 2 and 10 nm, the incremental pore volume distribution measured by nitrogen sorption, and
    wherein the mesoporous composite material has a cumulative pore volume distribution in $cm^3/g$ that has a minimum value for pores with a diameter of 10 nm or less of 0.2 $cm^3/g$, the cumulative pore volume distribution measured by nitrogen sorption.

15. The mesoporous composite carbonate material according to claim 14, wherein the maximum value in the incremental pore volume distribution in $cm^3/g$ of the mesoporous composite material occurring for pores with a diameter of 10 nm or less is 0.2 $cm^3/g$.

16. The mesoporous composite carbonate material according to claim 14, wherein the maximum value in the incremental pore volume distribution in $cm^3/g$ of the mesoporous composite material occurring for pores with a diameter of 10 nm or less is from 0.04 to 0.16 $cm^3/g$.

17. The mesoporous composite carbonate material according to claim 14, wherein the minimum value for cumulative pore volume distribution is at least 0.5 $cm^3/g$.

18. A method to produce a mesoporous composite carbonate material, the method comprising the steps of:
    preparing a powder phase comprising MgO and a second component, wherein the second component is $Ca(OH)_2$ or CaO, and wherein an amount of the second component is from >0 to 50 wt %; and
    reacting MgO and the second component with alcohol in a $CO_2$ atmosphere at a pressure above atmospheric pressure and a temperature between 40° C. and a boiling temperature of the alcohol,
    wherein the produced mesoporous composite carbonate material comprises X-ray amorphous and anhydrous magnesium carbonate and the second component, and
    wherein a maximum value in an incremental pore volume distribution in $cm^3/g$ of the produced mesoporous composite material occurs for pores with a diameter of 10 nm or less, the incremental pore volume distribution measured by nitrogen sorption, and
    wherein the produced mesoporous composite material has a cumulative pore volume distribution in $cm^3/g$ that has a minimum value for pores with a diameter of 10 nm or less of 0.2 $cm^3/g$, the cumulative pore volume distribution measured by nitrogen sorption.

19. The method according to claim 18, wherein the maximum value in the incremental pore volume distribution in cm³/g of the mesoporous composite material occurring for pores with a diameter of 10 nm or less is 0.2 cm³/g.

20. The method according to claim 18, wherein the maximum value in the incremental pore volume distribution in cm³/g of the mesoporous composite material occurring for pores with a diameter of 10 nm or less is from 0.04 to 0.16 cm³/g.

21. The method according to claim 18, wherein the minimum value for cumulative pore volume distribution is at least 0.5 cm³/g.

* * * * *